United States Patent
Garrigues

(10) Patent No.: US 12,096,926 B2
(45) Date of Patent: Sep. 24, 2024

(54) KNOTLESS ANCHOR TEMPORARY SUTURE CAPTURE

(71) Applicant: Medos International Sarl, Le Locle (CH)

(72) Inventor: Grant Garrigues, Chicago, IL (US)

(73) Assignee: Medos International Sarl, Le Locle (CH)

( * ) Notice: Subject to any disclaimer, the term of this patent is extended or adjusted under 35 U.S.C. 154(b) by 246 days.

(21) Appl. No.: 17/573,971

(22) Filed: Jan. 12, 2022

(65) Prior Publication Data
US 2023/0218287 A1 Jul. 13, 2023

(51) Int. Cl.
*A61B 17/04* (2006.01)

(52) U.S. Cl.
CPC .. *A61B 17/0401* (2013.01); *A61B 2017/0409* (2013.01); *A61B 2017/0414* (2013.01); *A61B 2017/0445* (2013.01); *A61B 2017/0464* (2013.01)

(58) Field of Classification Search
CPC .... A61B 2017/0409; A61B 2017/0414; A61B 2017/0445; A61B 2017/0464
See application file for complete search history.

(56) References Cited

U.S. PATENT DOCUMENTS

| | | | |
|---|---|---|---|
| 5,928,244 A | 7/1999 | Tovey et al. | |
| 6,007,566 A * | 12/1999 | Wenstrom, Jr. | .... A61B 17/0401 606/232 |
| 6,508,830 B2 | 1/2003 | Steiner | |
| 7,416,556 B2 * | 8/2008 | Jackson | ............. A61B 17/0487 606/232 |
| 9,023,082 B2 | 5/2015 | Wolf | |
| 9,173,652 B2 | 11/2015 | Lombardo et al. | |
| 9,265,494 B2 | 2/2016 | Hester et al. | |
| 9,277,911 B2 | 3/2016 | Hernandez | |
| 9,463,010 B2 * | 10/2016 | Gittings | ............. A61B 17/0401 |
| 9,763,719 B2 | 9/2017 | Snyder et al. | |
| 9,936,940 B2 | 4/2018 | Palese et al. | |

(Continued)

FOREIGN PATENT DOCUMENTS

WO   WO-2016186854 A1   11/2016
WO   WO-2016205876 A1   12/2016

OTHER PUBLICATIONS

International Search Report and Written Opinion for International Patent Application No. PCT/EP2023/050608 mailed Apr. 11, 2023.

*Primary Examiner* — Alexander J Orkin
(74) *Attorney, Agent, or Firm* — Mintz Levin Cohn Ferris Glovsky and Popeo, P.C.

(57) ABSTRACT

Various exemplary devices, systems, and methods for knotless anchor temporary suture capture are provided. In general, an inserter tool is configured for knotless anchor insertion in a soft tissue repair surgical procedure. The inserter tool is configured to insert an anchor into a bone of a patient to secure a soft tissue relative to the bone. A suture coupled to the soft tissue is secured relative to the bone by being trapped between an exterior surface of the anchor and a bone surface defining a hole in the bone in which the anchor is positioned. The inserter tool and the anchor are configured to cooperate with one another to temporarily capture and lock the suture with respect to the anchor and the inserter tool before the anchor is secured in the bone hole.

15 Claims, 14 Drawing Sheets

(56) References Cited

U.S. PATENT DOCUMENTS

| | | | |
|---|---|---|---|
| 10,034,742 B2 | 7/2018 | Diduch et al. | |
| 10,188,378 B2 | 1/2019 | Lunn et al. | |
| 10,463,357 B2 | 11/2019 | Gustafson et al. | |
| 10,820,899 B2 | 11/2020 | George et al. | |
| 2003/0105489 A1* | 6/2003 | Eichhorn | A61B 17/0401 606/232 |
| 2006/0253119 A1* | 11/2006 | Berberich | A61B 17/0401 606/232 |
| 2006/0282083 A1* | 12/2006 | Fanton | A61B 17/0401 606/232 |
| 2008/0167660 A1 | 7/2008 | Moreau et al. | |
| 2012/0053624 A1* | 3/2012 | Sojka | A61B 17/0485 606/232 |
| 2012/0059415 A1* | 3/2012 | Sklar | A61B 17/0401 606/232 |
| 2013/0144334 A1* | 6/2013 | Bouduban | A61B 17/0401 606/232 |
| 2014/0257381 A1* | 9/2014 | Palese | A61B 17/0401 606/232 |
| 2014/0364906 A1* | 12/2014 | Palese | A61B 17/0401 606/232 |
| 2016/0113756 A1 | 4/2016 | Diduch et al. | |
| 2016/0310125 A1* | 10/2016 | Spivey | A61B 17/0401 |
| 2017/0311943 A1 | 11/2017 | Housman et al. | |
| 2018/0235595 A1 | 8/2018 | Palese et al. | |
| 2018/0235746 A1* | 8/2018 | Pilgeram | A61B 17/0401 |
| 2018/0256148 A1* | 9/2018 | Miller | A61B 17/0401 |
| 2018/0338755 A1 | 11/2018 | Palese et al. | |
| 2019/0090868 A1 | 3/2019 | Bracy et al. | |
| 2020/0155137 A1 | 5/2020 | Brunsvold et al. | |
| 2021/0338223 A1 | 11/2021 | Patel et al. | |
| 2021/0338224 A1 | 11/2021 | Patel et al. | |
| 2021/0338225 A1 | 11/2021 | Patel et al. | |
| 2023/0149008 A1* | 5/2023 | Su | A61F 2/0811 606/232 |

* cited by examiner

KNOTLESS ANCHOR TEMPORARY SUTURE CAPTURE

FIELD

The present disclosure generally relates to knotless anchor temporary suture capture.

BACKGROUND

A variety of injuries and conditions require repair of soft tissue damage, or reattachment of soft tissue to bone and/or surrounding tissue. For example, when otherwise healthy tissue has been torn away from a bone, such as a labrum tearing away from a glenoid (shoulder instability), surgery is often required to reattach the tissue to the bone, to allow healing in the proper position to occur. A number of devices and methods have been developed for performing these surgical repairs. Some of the more successful methods including the use of suture fixation members, such as suture anchors, which typically include an anchor body having a suture attachment feature and a tissue or bone engaging feature for retaining the suture anchor within or adjacent to the tissue or bone. Depending on the specific injury, one or more suture anchors connected to, or interconnected by, one or more segment of suture, may be used to perform the repair.

Surgery can also be required when a tear occurs in the substance of a single type of tissue. Sutures can also be used in conjunction with one or more suture anchors to repair such tissue tears. Sutures can be fastened to suture anchors and to tissue using knots tied by the surgeon during a repair procedure, or using "knotless" devices and methods, where one or more anchors and one or more sutures can be connected and tensioned without the surgeon needing to tie knots during the surgery. Knotless anchoring is of particular utility for minimally invasive surgeries, such as endoscopic or arthroscopic repairs, where the surgeon remotely manipulates the suture at the surgical site using tools inserted through a small diameter cannula, an endoscopic tube, or otherwise percutaneously, which can make the knotting process difficult and tedious. Furthermore, the knot itself can be irritating to surrounding tissues. However, while knotless anchors can be very effective in reattaching soft tissue to bone, the small size of the anchor and patient anatomy can make it difficult to locate and insert the anchor into the bone hole. Additionally, visualization of the hole can be difficult due to challenging angles and the tight nature of the joint space.

Accordingly, there remains a need for improved devices, systems, and methods for knotless anchors.

SUMMARY

In general, devices, systems, and methods for knotless anchor temporary suture capture are provided.

In one aspect, a surgical system is provided that in one embodiment includes an anchor and an inserter tool. The anchor is configured to be implanted in a bone hole, and the anchor has a pair of slots formed therein. The inserter tool includes an outer shaft and an inner shaft. The anchor is configured to be releasably coupled to the inserter tool. With the anchor releasably coupled to the inserter tool, the inner shaft is configured to selectively be in one of a first position, in which the inner shaft obstructs the pair of slots, and a second position, in which the inner shaft does not obstruct the pair of slots. The inner shaft in the second position is configured to extend distally beyond the anchor and the outer shaft and, thereafter, the outer shaft is configured to translate axially in a distal direction relative to the inner shaft and thereby cause the anchor to translate axially in the distal direction into the bone hole.

The surgical system can vary in any number of ways. For example, the anchor can be configured to be releasably coupled to a suture with the suture extending through the slots of the anchor and being seated in a suture retention channel of the inner shaft, the suture can be in a locked position relative to the anchor with the inner shaft being in the first position, and the inner shaft changing from the first position to the second position can be configured to cause the suture to move from the locked position to an unlocked position relative to the anchor. The inner shaft in the second position translating axially in the distal direction can be configured to push the suture out of the slots. The surgical system can also include the suture.

For another example, each of the slots can have an open distal end and a closed proximal end. The inner shaft changing from the second position to the first position can be configured to urge a suture extending through the slots to move proximally within the slots, and the inner shaft translating axially in a distal direction can be configured to move the suture distally within the slots and out of the open distal ends of the slots. Each of the slots can have an L-shape or each of the slots can have a helical shape.

For yet another example, the inner shaft can have a pair of distal arms; the anchor can have a pair of distal arms; with the inner shaft in the first position, the distal arms of the inner shaft can be misaligned from the distal arms of the anchor; and with the inner shaft in the second position, the distal arms of the inner shaft can be aligned with the distal arms of the anchor.

For still another example, the inner shaft can have a pair of distal arms; with the inner shaft in the first position, the distal arms of the inner shaft can be aligned with the slots of the anchor; and with the inner shaft in the second position, the distal arms of the inner shaft can be misaligned from the slots of the anchor.

For another example, in the first position the inner shaft can not extend distally beyond the anchor.

For yet another example, after the translation of the outer shaft, the outer shaft and the inner shaft can be configured to simultaneously translate axially in a proximal direction relative to the anchor in the bone hole.

For another example, prior to the translation of the outer shaft in the distal direction, a distal end of the outer shaft can abut a proximal end of the anchor having the inner shaft positioned within an inner lumen thereof.

In another embodiment, a surgical system includes an anchor, an inner shaft, and an outer shaft. The anchor is configured to be implanted in a bone hole, and the anchor has a pair of distal arms that define a pair of slots therebetween. The inner shaft is configured to be seated in an inner lumen of the anchor, the inner shaft has a pair of distal arms, and the anchor is configured to be rotated relative to the inner shaft with the inner shaft within the inner lumen of the anchor such that the distal arms of the inner shaft change from being aligned with the distal arms of the anchor and misaligned from the slots of the anchor to being misaligned from the distal arms of the anchor and aligned with the slots of the anchor. The outer shaft is configured to longitudinally translate distally relative to the inner shaft and the anchor and thereby move the anchor distally into the bone hole.

The surgical system can have any number of variations. For example, the inner shaft can be configured to longitudinally move into the bone hole prior to the outer shaft being longitudinally translated distally relative to the inner shaft and the anchor. The longitudinal movement of the inner shaft can be configured to push a suture seated in the slots of the anchor out of the slots and into the bone hole.

For another example, the anchor can be configured to be releasably coupled to a suture with the suture extending through the slots of the anchor and being seated in a suture retention channel of the inner shaft, the suture can be in a locked position relative to the anchor with the distal arms of the inner shaft being misaligned from the distal arms of the anchor and aligned with the slots of the anchor, and the suture can be in an unlocked position relative to the anchor with the distal arms of the inner shaft being aligned with the distal arms of the anchor and misaligned from the slots of the anchor. The surgical system can also include the suture.

For yet another example, prior to the distal translation of the outer shaft, a distal end of the outer shaft can abut a proximal end of the anchor having the inner shaft positioned within the inner lumen thereof.

For still another example, each of the slots can have an L-shape or each of the slots can have a helical shape.

In another aspect, a surgical method is provided that in one embodiment includes rotating an outer shaft of an inserter tool and an anchor releasably coupled to the inserter tool relative to an inner shaft of the inserter tool. The rotation of the outer shaft and the anchor causes a suture extending through slots of the anchor to move from a locked position to an unlocked position. The rotation of the outer shaft and the anchor causes the suture to be pushed out of the slots and into a bone hole. The surgical method also includes, after the rotation of the outer shaft and the anchor, longitudinally translating the outer shaft distally relative to the inner shaft, thereby pushing the anchor into the bone hole to secure the anchor therein.

The surgical method can vary in any number of ways. For example, the rotation of the outer shaft and the anchor can be in a first direction; the surgical method can also include, prior to the rotation of the outer shaft and the anchor in the first direction, rotating the outer shaft and the anchor in a second direction that is opposite to the first direction; the rotation of the outer shaft and the anchor in the second direction can be relative to the inner shaft; and the rotation of the outer shaft and the anchor in the second direction can cause the suture extending through slots of the anchor to move from the unlocked position to the locked position. The rotation of the outer shaft and the anchor in the first direction can cause distal arms of the inner shaft to change from being aligned with the slots of the anchor to being misaligned from the slots of the anchor, and the rotation of the outer shaft and the anchor in the second direction can cause the distal arms of the inner shaft to change from being misaligned from the slots of the anchor to being aligned with the slots of the anchor. The rotation of the outer shaft and the anchor in the first direction can cause the distal arms of the inner shaft to change from being misaligned from distal arms of the anchor to being aligned with the distal arms of the anchor, and the rotation of the outer shaft and the anchor in the second direction can cause the distal arms of the inner shaft to change from being aligned from the distal arms of the anchor to being misaligned from the distal arms of the anchor.

For another example, the rotation of the outer shaft and the anchor in the first direction can cause distal arms of the inner shaft to change from being aligned with the slots of the anchor to being misaligned from the slots of the anchor. The rotation of the outer shaft and the anchor in the first direction can cause the distal arms of the inner shaft to change from being misaligned from distal arms of the anchor to being aligned with the distal arms of the anchor, and the rotation of the outer shaft and the anchor in the second direction can cause the distal arms of the inner shaft to change from being aligned from the distal arms of the anchor to being misaligned from the distal arms of the anchor.

For yet another example, the inner shaft can be positioned within an inner lumen of the anchor during the rotation of the outer shaft and the anchor and during the longitudinal translation of the outer shaft.

For still another example, the surgical method can also include, after the longitudinal translation of the outer shaft, longitudinally translating the outer and inner shafts proximally relative to the anchor such that the inner shaft is removed from the bone hole and the anchor and the suture remain in the bone hole.

For yet another example, each of the slots can have an L-shape or each of the slots can have a helical shape.

BRIEF DESCRIPTION OF DRAWINGS

This disclosure will be more fully understood from the following detailed description taken in conjunction with the accompanying drawings, in which.

DETAILED DESCRIPTION

Figure 1:
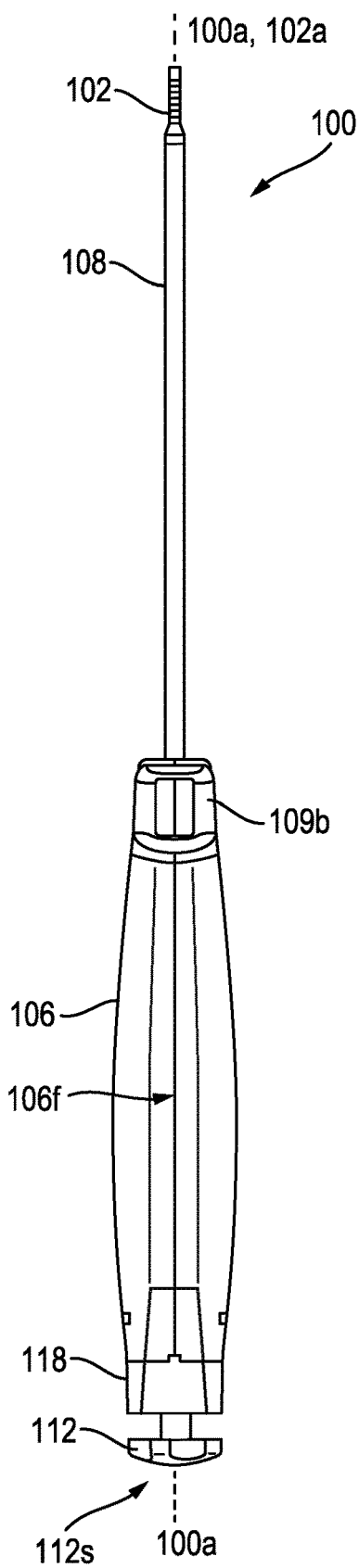
FIG. 1 is a side view of one embodiment of an inserter tool having a suture anchor releasably coupled thereto.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary devices, systems, and methods for knotless anchor temporary suture capture are provided. In general, an inserter tool is configured for knotless anchor insertion in a soft tissue repair surgical procedure. The inserter tool is configured to insert an anchor into a bone of a patient to secure a soft tissue relative to the bone. A suture coupled to the soft tissue is secured relative to the bone by being trapped between an exterior surface of the anchor and a bone surface defining a hole in the bone in which the anchor is positioned. The anchor therefore allows the suture to be secured in position without needing to be knotted, which can be time consuming and/or difficult to perform during surgery because of small suture diameter, limited working area at a joint space, a wet surgical environment, and/or limited visualization at the surgical site due to challenging angles and the tight nature of the joint space.

The inserter tool is configured to have each of the suture and the anchor releasably coupled thereto and, with the suture and the anchor releasably coupled thereto, to insert the suture and the anchor into the bone hole. The inserter tool is configured to position the suture in the bone hole before the anchor is secured in the bone hole. In an exemplary embodiment, the inserter tool includes a suture retention channel configured to releasably retain the suture therein, and the anchor includes a pair of slots configured to releasably seat the suture therein. The suture retention channel and the pair of slots are configured to cooperate with one another to temporarily capture and lock the suture with respect to the anchor and the inserter tool before the anchor is secured in the bone hole. The anchor and the suture may thus be advanced as a unit into position relative to a bone in which the anchor will be secured without the suture becoming dislodged from the anchor or the inserter tool. The inserter tool is configured to move relative to the anchor to unlock the suture with respect to the anchor and the inserter tool after the anchor and the suture are in position relative to the bone before the anchor is secured in the bone hole. With the suture unlocked, the inserter tool can be used to push the suture into the bone hole before the anchor is advanced into the bone hole. The suture may thus be tensioned and positioned in the bone hole before the anchor secures the suture within the bone hole. Furthermore, the anchor including the pair of slots to releasably seat the suture helps reduce material of the anchor, which, especially in areas where bone is limited, may limit anchor burden, weakening of the bone, and disruption of the bony anatomy.

In an exemplary embodiment, the suture has a U-shape before and after the anchor is advanced into and secured in the bone hole. In the U-shape, each of the suture's legs extend longitudinally along opposed sides of the anchor, and an intermediate portion of the suture that connects the legs extends along the anchor's distal end so as to loop around the anchor's distal end. The U-shape configuration of the suture relative to the anchor may maximize a length of the suture that the anchor presses against to fix the suture in position relative to the bone, which may help ensure that the soft tissue coupled to the suture remains in a fixed position relative to the bone to facilitate healing.

The inserter tool is configured to advance the anchor into the bone hole by longitudinally translating the anchor in a distal direction into the bone hole, such as by hitting the inserter tool with a mallet, hammer, or other tool, thereby trapping the suture between the exterior surface of the anchor and the bone surface defining the bone hole. After the anchor has been inserted into the bone, the inserter tool is configured to be longitudinally translated in a proximal direction to be removed from the patient's body with the anchor and the suture remaining in the bone. Decoupling the inserter tool from the suture and the anchor by longitudinally translating the inserter tool along its longitudinal axis may be less time consuming and/or may require less user-applied force than other methods of decoupling a tool from an implanted anchor that include rotating the tool about its longitudinal axis. Unlike longitudinally translating the inserter tool for removal, rotating the tool for removal can risk rotating the anchor and/or unintended off axis loading, which can cause the anchor to become less securely positioned in the bone and/or can cause damage to the suture and/or to the anchor.

The systems, devices, and methods described herein have applicability in a variety of surgical procedures for soft tissue repair, such as in a tissue repair surgical procedure at a joint such as a shoulder, a knee, or a hip.

Figure 2:
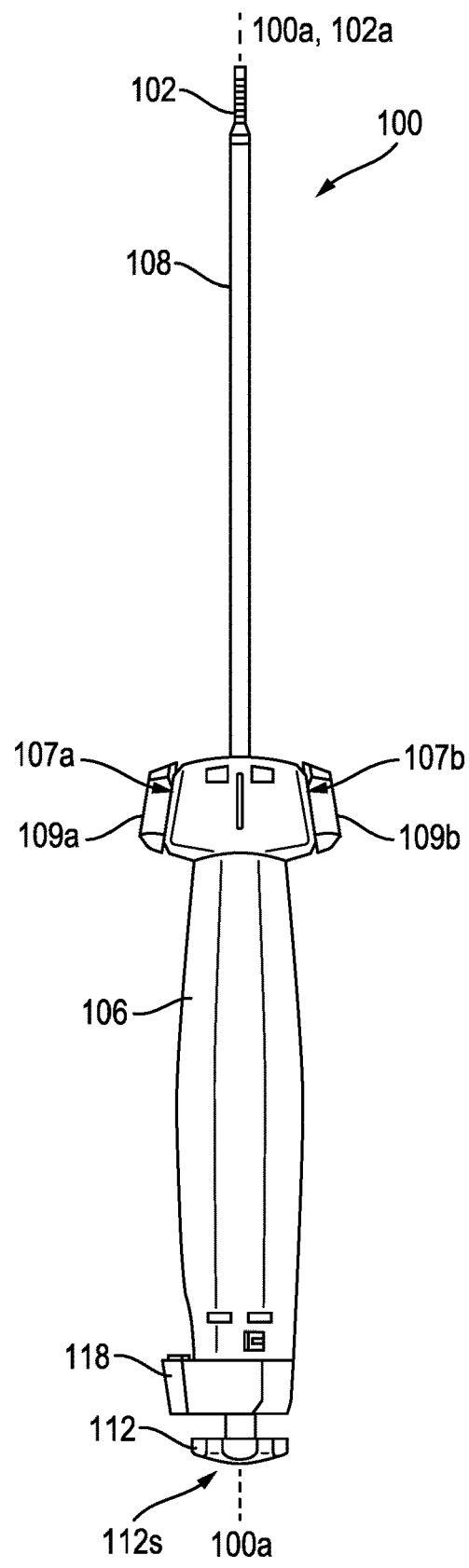
FIG. 2 is another side view of the inserter tool and anchor of FIG. 1.
Figure 3:
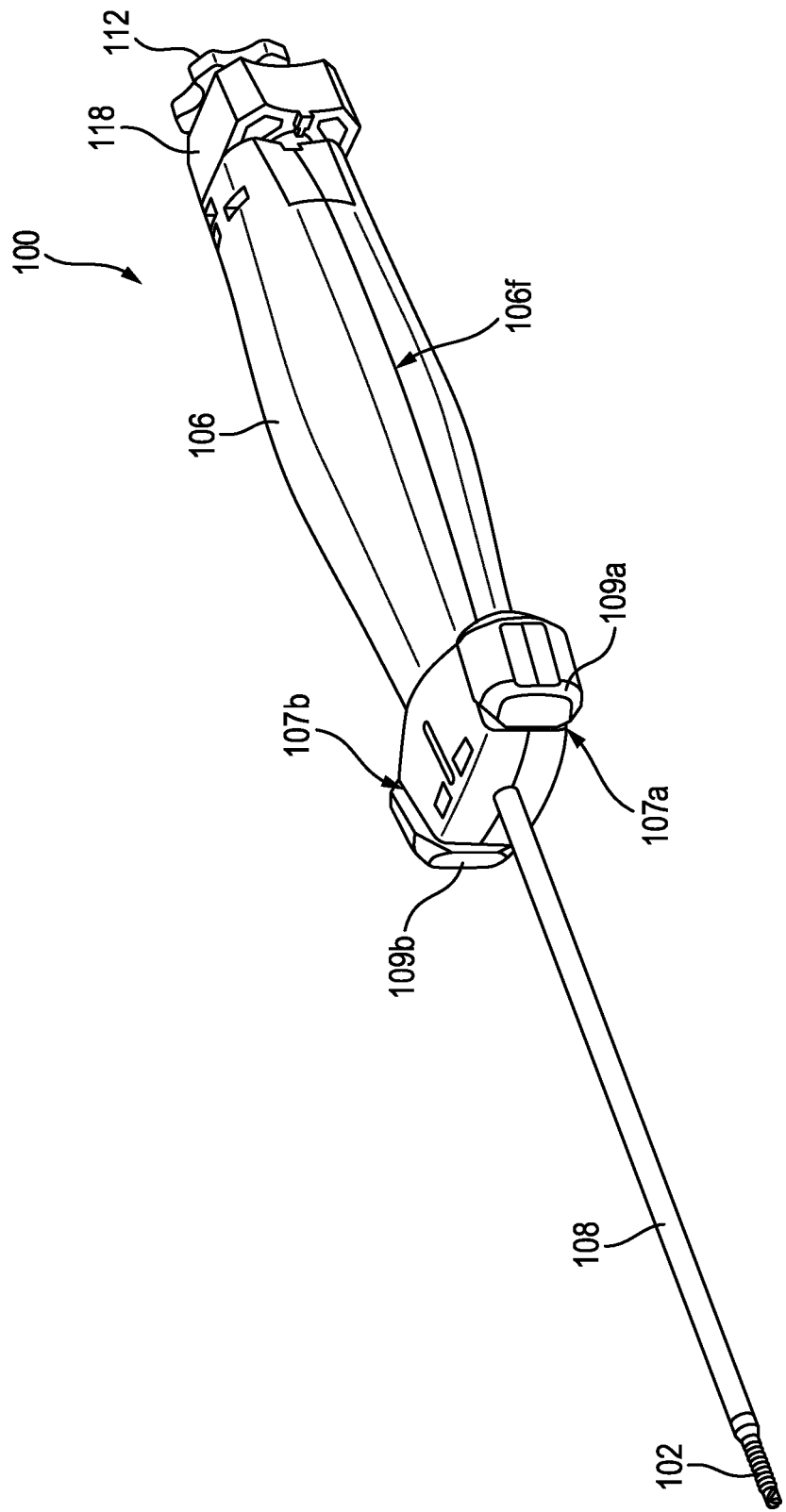
FIG. 3 is a perspective view of the inserter tool and anchor of FIG. 1.
Figure 4:
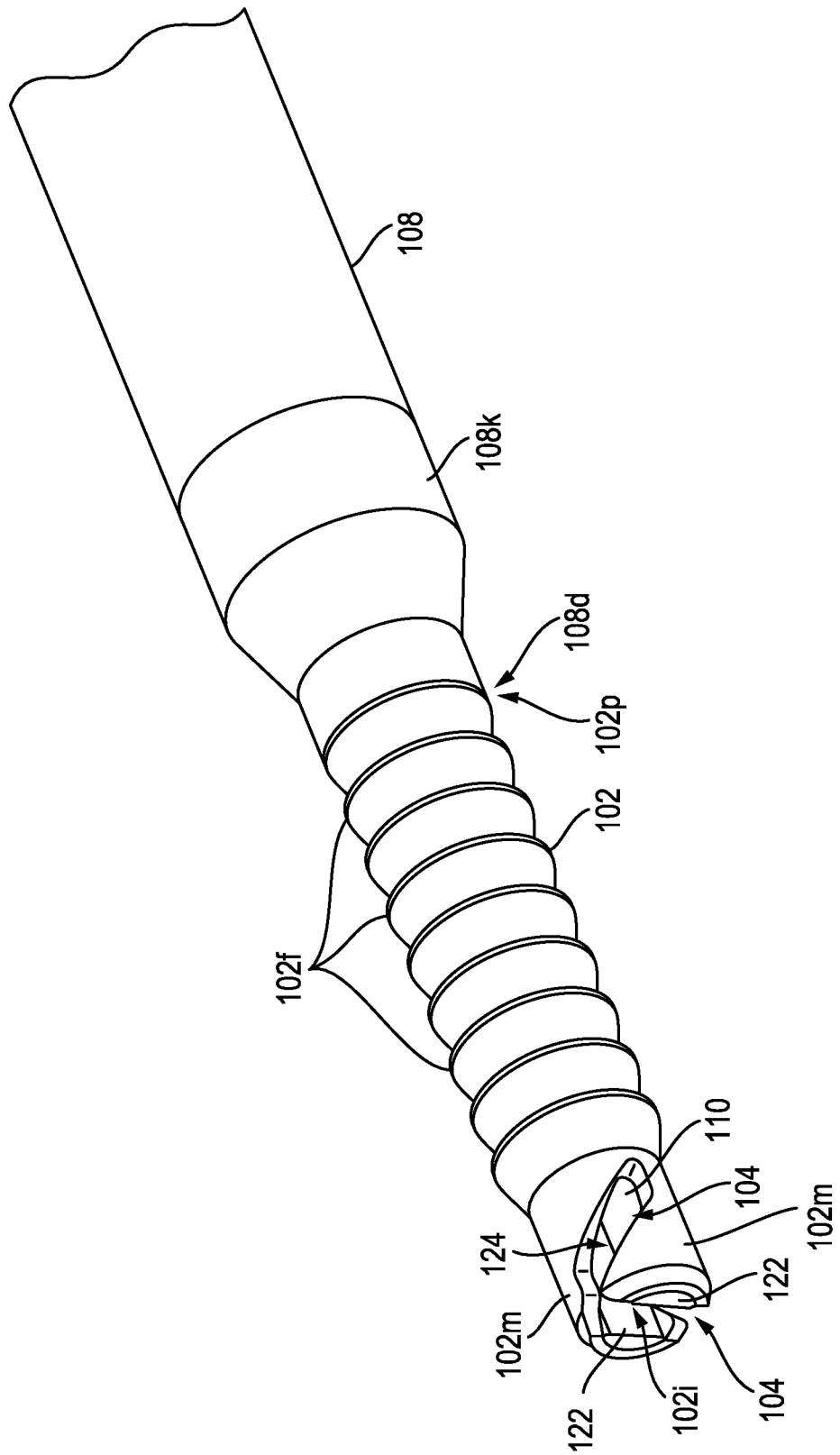
FIG. 4 is a perspective view of the anchor and a distal portion the inserter tool of FIG. 1.
Figure 5:
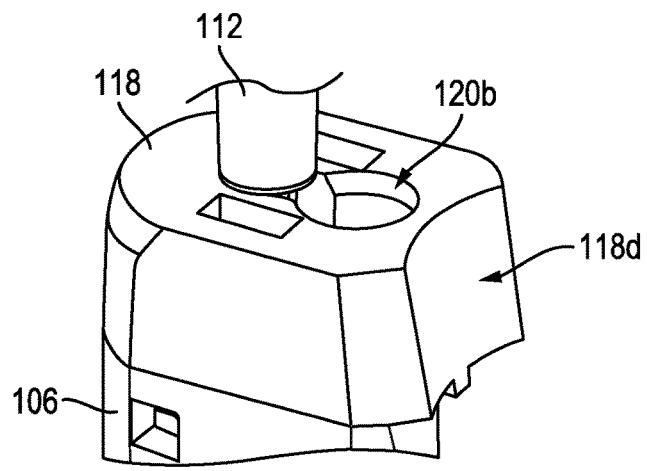
FIG. 5 is a perspective view of a portion of the inserter tool of FIG. 1 with a locking mechanism of the inserter tool in a locked position.

FIGS. 1-3 illustrate one embodiment of an inserter tool 100 (also referred to herein as an "inserter"). The inserter tool 100 is configured for use in knotless anchor insertion in a soft tissue repair surgical procedure. In general, the inserter tool 100 is configured to insert an anchor 102 into a bone of a patient to secure a soft tissue relative to the bone. As shown in FIG. 4, an inner lumen 102$i$ extends through the anchor 102 such that the anchor 102 is cannulated. A plurality of bone-engaging surface features 102$f$ are formed on an exterior surface of the anchor 102. The bone-engaging surface features 102$f$ are configured to engage bone to retain the anchor 102 in the bone, e.g., to engage a surface of bone defining a hole in bone in which the anchor 102 is positioned. The bone-engaging surface features 102$f$ include a plurality of ribs each extending circumferentially around the anchor 102 at different axial positions along the anchor's longitudinal length. The bone-engaging surface features 102$f$ can, however, have another configuration, such as a plurality of barbs or other form of protrusions formed on the anchor's exterior surface. The bone-engaging surface features 102$f$ are also configured to engage a suture against the bone to help secure the suture relative to the bone.

As shown in FIG. 4, the anchor 102 includes a pair of opposed slots 104 formed therein. As discussed further below, the slots 104 are configured to releasably seat a suture therein. As also discussed further below, the anchor 102 and the inner shaft 110 are configured to cooperate with one another to create a temporary enclosure with the suture being seated and captured in the slots 104.

The slots 104 are independent from one another and do not intersect one another. Each slot 104 extends proximally from a distal end of the anchor 102 and is in communication with the inner lumen 102$i$ of the anchor 102 and with a distal opening of the inner lumen 102$i$ at a distal end of the anchor 102. Each slot 104 extends transverse to a longitudinal axis 102$a$ of the anchor 102. With the anchor 102 releasably coupled to the inserter tool 100, the longitudinal axis 102$a$ of the anchor 102 is coaxial with a longitudinal axis 100$a$ of the inserter tool 100, which is also the longitudinal axis of each of an outer shaft 108 and an inner shaft 110 of the inserter tool 100. The slots 104 thus extend transverse to the longitudinal axes 100$a$ of the inserter tool 100, the outer shaft 108, and the inner shaft 110.

Each slot 104 in this illustrated embodiment has a helical shape with the slots 104 extending helically partially around the anchor 102. The slots 104 spiral in a same direction. In this illustrated embodiment, the slots 104 spiral counterclockwise in a distal to proximal direction but could instead spiral clockwise in a distal to proximal direction.

The slot 104 in the anchor 102 are each located entirely distal to the anchor's bone-engaging features 102$f$. The slots 104 therefore do not interfere with the engagement of the bone-engaging features 102$f$ with bone. The anchor 102 accordingly has a proximal portion including the bone-engaging features 102$f$ but not including the slots 104, and has a distal portion including the slots 104 but not including the bone-engaging features 102$f$.

The anchor 102 includes a pair of opposed distal arms 102$m$ that are located between the slots 104. The anchor's distal arms 102$m$ are thus located in the distal portion of the anchor 102 that includes the slots 104 but not the bone-engaging features 102$f$.

The anchor 102 can be absorbable or non-absorbable. The anchor 102 can be made from any of a variety of materials, e.g., Polyether ether ketone (PEEK), Polylactic acid or polylactide (PLA), BIOCRYL®, BIOCRYL® RAPIDE®, titanium, ceramics, carbon fiber, stainless steel, etc. The anchor 102 can be formed by a variety of techniques, for example by machining, molding, metal injection molding, overmolding, or by a post-molding process such as post-molding machining.

The inserter 100 includes a handle 106. The handle 106 is configured to be held by hand during use of the inserter 100. In robotic surgical implementations, the handle 106 can be held by a mechanical member of the robotic surgical system. The handle 106 has a generally cylindrical, distally-tapering shape in this illustrated embodiment but can have any of a variety of shapes.

The outer shaft 108 of the inserter 100 extends distally from the handle 106, and the inner shaft 110 (also referred to herein as an "inserter shaft") of the inserter 100 also extends distally from the handle 106. The handle 106 has an inner lumen extending therethrough. The outer and inner shafts 108, 110 are positioned in the inner lumen of the handle 106 and extend distally out of the inner lumen of the handle 106. Proximal ends of one or both of the outer and inner shafts 108, 110 can be located within the inner lumen of the handle 106, or one or both of the outer and inner shafts 108, 110 can extend proximally beyond the handle 106 such that the respective proximal ends of the outer and inner shafts 108, 110 are located proximal to the handle 106. For example, as in this illustrated embodiment, the proximal end of the inner shaft 110 can be attached to the handle 106, and the proximal end of the outer shaft 108, also referred to herein as a "push tube," can be located within the inner lumen of the handle 106. For another example, the proximal end of the inner shaft 110 can be attached to the handle 106, and the proximal end of the outer shaft 108 can be located proximal to the handle 106.

The handle 106 in this illustrated embodiment includes facets 106$f$ on opposed sides, e.g., left and right sides, thereof. The facets 106$f$ are configured to help a user with grip and fine motor movements.

The handle 106 in this illustrated embodiment includes a suture retention member configured to releasably retain a suture to hold the suture in a desired position at a desired tension. A suture is traditionally retained using a hemostat. The inserter tool 100 including a suture retention member may eliminate the need to use any hemostats for the suture. The suture retention member is located at a distal end of the handle 106 but can be located elsewhere.

Various embodiments of suture retention members are further described, for example, in U.S. Pat. Pub. No. 2021/0338223 entitled "Knotless Anchor Insertion" published Nov. 4, 2021, which is hereby incorporated by reference in its entirety. The suture retention member in this illustrated embodiment includes a pair of grooves 107$a$, 107$b$ on opposed sides, e.g., left and right sides, of the handle 106. Providing the suture retention member on opposed sides of the handle 106 may help accommodate use of the inserter tool 100 by left-handed and right-handed users and/or may facilitate engaging the suture with one of the suture retention members regardless of an orientation at which the inserter tool 100 is being held and an angle of the suture's approach to the handle 106. The inserter tool 100 can, however, include only one suture retention member, e.g., on either the left or right side of the handle.

A first one of the suture retention grooves 107a is defined between the handle 106 and a first elastomeric cleat 109a fixedly attached to the handle 106. A second one of the suture retention grooves 107b is defined between the handle 106 and a second elastomeric cleat 109b fixedly attached to the handle 106. The first and second elastomeric cleats 109a, 109b are each made from an elastomeric material, such as rubber or other polymer. The handle 106 is made from a rigid, non-elastomeric material, such as a plastic such as polycarbonate or other plastic; metal (e.g., stainless steel, titanium, etc.); polytetrafluoroethylene (PTFE); or other biocompatible material. The grooves 107a, 107b are thus each located at a junction between an elastomeric material and a rigid material. The elastomeric material of the first and second elastomeric cleats 109a, 109b allows a width of the groove 107a, 107b associated therewith to dynamically increase to adjust to a size and shape of the suture being seated therein to securely hold the suture in the groove 107a, 107b, gripped between the elastomeric material and the rigid material. The suture retention member is thus self-adjusting. Different sutures have different sizes and shapes, and the first and second elastomeric cleats 109a, 109b are each configured to dynamically adjust to the particular size and shape of a suture being seated therein. The suture being securely held in the groove 107a, 107b may help the suture's tension be maintained, e.g., without being lessened, while the suture is retained by the suture retention member. When the suture is released from the groove 107a, 107b, the elastomeric cleat 109a, 109b is no longer gripping the suture and is thus allowed to return to its original, smaller width as the elastomeric material elastically returns to its original configuration.

The suture retention member is located at a hammerhead shaped portion of the inserter tool 100 defined by the handle 106 and the elastomeric cleats 109a, 109b. A proximal surface of the hammerhead shaped portion defined by a proximal surface of the handle 106 and a proximal of each of the elastomeric cleats 109a, 109b, extends radially outward and tapers distally. The tapering is configured to urge a suture along the proximal surface of the handle 106 toward one of the elastomeric cleats 109a, 109b for seating the groove 107a, 107b associated therewith. Each of the elastomeric cleats 109a, 109b has a beveled edge facing its associated groove 107a, 107b, which may also help urge the suture into the groove 107a, 107b.

The inserter 100 also includes a strike cap 112 that extends proximally from the handle 106. A distal end of the strike cap 112 abuts the proximal end of the push tube 108 in the inserter's initial configuration, which may maximize transmission of a distal force applied to the strike cap 112 to the push tube 108 and thereby help efficiently distally advance the push tube 108 to distally advance the anchor 102 into a bone hole. However, the strike cap's distal end can be spaced a distance proximal to the push tube's proximal end, or the strike cap 112 can be integrally formed with the push tube 108. The strike cap 112 is configured to be struck with a mallet, hammer, or other tool on a proximal surface 112s thereof. The proximal surface 112s in this illustrated embodiment is convex curved, which may provide more feedback (compared to a flat surface) to a user striking the strike cap 112. The strike cap 112 can, however, have a flat surface, which may facilitate an even strike on the strike cap 112 and thus an evenly transmitted distal force from the strike cap 112 to the push tube 108.

The strike cap 112 has a six-lobed shape in this illustrated embodiment but can have another shape, such as circular, ovular, tri-lobed, four-lobed, five-lobed, square, rectangular, etc.

The proximal surface 112s of the strike cap 112 is exposed for striking by a mallet, hammer, or other tool. In other embodiments, an inserter tool can include a strike cap and a protective member configured to cover or hide at least the strike surface of the strike cap. The protective member may help prevent premature striking of the strike cap and/or any unintentional distal movement of the strike cap and thus any unintentional distal advancement of an anchor coupled to the inserter tool. In some embodiments the protective member can completely cover or hide the strike cap. Various embodiments of protective members are further described, for example, in previously mentioned U.S. Pat. Pub. No. 2021/0338223 entitled "Knotless Anchor Insertion" published Nov. 4, 2021.

As discussed further below, the strike cap 112 is configured as a knob configured to be rotated to move the outer shaft 108 and the anchor 102 relative to the inner shaft 110.

In other embodiments, instead of a rotatable knob being configured to move the outer shaft 108 and the anchor 102, another mechanism can be used such as a depressible button at the handle 106 being configured to be depressed to cause the movement of the outer shaft 108 and the anchor 102. For another example, a lever at the handle 106 can be configured to be moved to cause the movement of the outer shaft 108 and the anchor 102.

An inner lumen extends through the outer shaft 108 such that the outer shaft 108 is cannulated. In the initial configuration of the inserter 100, which is shown in FIGS. 1-4, the inner shaft 110 is seated in the inner lumen 102i of the anchor 102 and in the inner lumen of the outer shaft 108. As discussed further below, the inner shaft 110 is configured to extend distally beyond the outer shaft 108 and the anchor 102 to facilitate suture manipulation, and the anchor 102 and the outer shaft 108 are each configured to be movable relative to the inner shaft 110 to facilitate delivery of the anchor 102 into a bone hole.

A distal end 108d of the outer shaft 108 is located proximal to a proximal end 102p of the anchor 102. In an exemplary embodiment, as shown in FIG. 4, the outer shaft's distal end 108d abuts the anchor's proximal end 102p in the inserter's initial configuration, which may facilitate extension of the inner shaft 110 distally beyond the outer shaft 108 and the anchor 102 and may maximize transmission of a distal force applied to the push tube 108 to the anchor 102 and thereby help efficiently distally advance the anchor 102 into a bone hole. The proximal end 102p of the anchor 102 include a mating element (obscured in FIG. 4) configured to releasably mate to a mating feature (obscured in FIG. 4) at the distal end 108d of the outer shaft 108. The mating of the mating element and the mating feature is configured to releasably hold the anchor 102 and the outer shaft 108 together until after the anchor 102 has been implanted in bone which, as discussed further below, facilitate the inner shaft's extension distally beyond the outer shaft 108 and the anchor 102. The mating element and the mating feature can have a variety of configurations. For example, one of the mating element and the mating feature can include one or more depressions, and the other one of the mating element and the mating feature can include one or more protrusions each configured to releasably seat in one of the one or more depressions. A shape and size of each of the protrusions corresponds to a shape and size of the depression in which the protrusion is releasably seated, e.g., the protrusions and the depressions each having semi-spherical shapes, such that the protrusions are releasably snapped into the depressions.

The outer shaft 108 includes a distal knob 108k that tapers distally and defines the distal end 108d of the outer shaft 108. The distal tapering of the knob 108k allows a proximal portion of the outer shaft 108 to have a larger diameter than the distal end 108d of the outer shaft 108 such that the smaller diameter at the distal end 108d of the outer shaft 108 corresponds to a diameter of the anchor 102 at its proximal end 102p, which may help the outer shaft 108 releasably mate to the anchor 102 and efficiently apply distally-directed force to the anchor 102.

Figure 6:
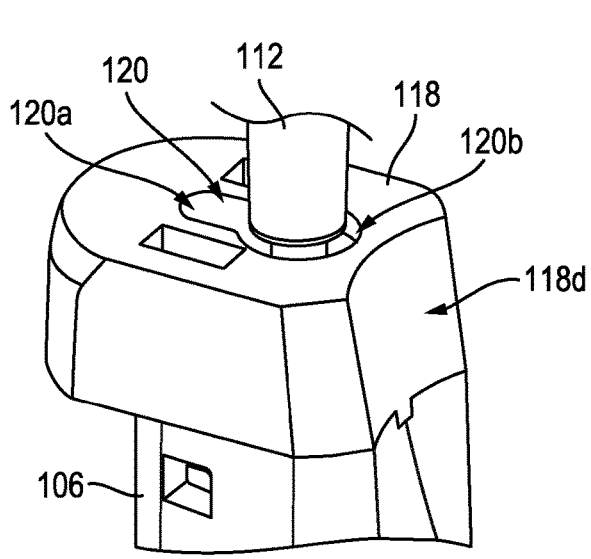
FIG. 6 is a perspective view of a portion of the inserter tool of FIG. 5 with the locking mechanism in an unlocked position.
Figure 7:
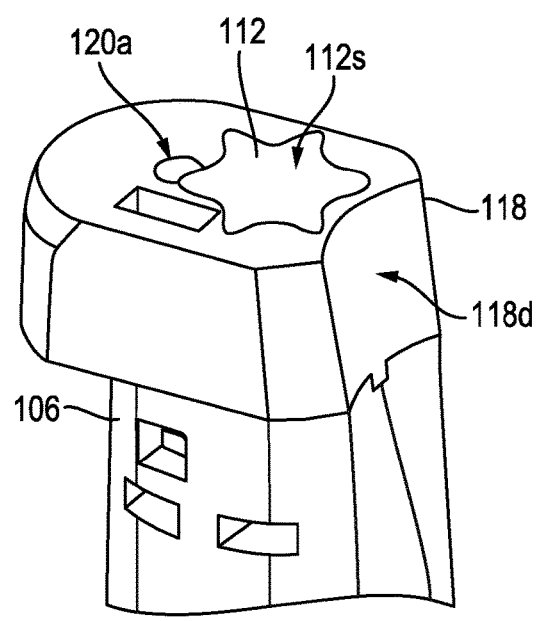
FIG. 7 is a perspective view of a portion of the inserter tool of FIG. 6 with the locking mechanism after striking of a strike cap of the inserter tool.

The inserter tool 100 includes a locking mechanism 118 configured to lock the outer shaft 108 such that the outer shaft 108 cannot move distally relative to the inner shaft 110 when the locking mechanism 118 is in a locked position. FIGS. 1-3 and 5 show the locking mechanism 118 in the locked position. FIGS. 6 and 7 show the locking mechanism 118 in an unlocked position, in which the outer shaft 108 is configured to move distally relative to the inner shaft 110. The locking mechanism 118 is configured to move from the locked position to the unlocked position by sliding relative to the outer shaft 108, the inner shaft 110, the strike cap 112, and the handle 106. The sliding movement of the locking mechanism 118 is lateral movement substantially perpendicular to the longitudinal axes of the outer and inner shafts 108, 110. The initial position of the locking mechanism 118 is the locked position, to help prevent premature distal translation of the outer shaft 108 relative to the inner shaft 110 and thus help prevent premature distal advancement of the anchor 102 relative to the inner shaft 110.

The locking mechanism 118 includes a depression 118d on a side thereof. The depression 118d is configured to communicate where a finger should be placed on the locking mechanism 118. The depression's surface is configured as a push surface on which a finger can be placed to push the locking mechanism 118 from the locked position to the unlocked position. A curvature of the depression 118d matches a curvature of the handle 106 adjacent to the locking mechanism 118 in the unlocked position. The matching curvature of the depression 118d and the handle 106 is configured to indicate to a user that the locking mechanism 118 has fully moved to the unlocked position.

The locking mechanism 118 includes a keyhole 120 formed therein in which the outer shaft 108 and the strike cap 112 are each configured to move. The keyhole 120 includes a reduced diameter portion 120a and an enlarged diameter portion 120b. With the locking mechanism 118 in the locked position, the outer shaft 108 extends through the reduced diameter portion 120a and the strike cap 112 is located proximal to the keyhole 120. The diameter of the reduced diameter portion 120a is less than a diameter of the strike cap 112 at least at the distal end of the end cap 112. The strike cap 112 thus cannot move distally into the keyhole 120, thereby preventing the outer shaft 108 from moving distally by the strike cap 112 being struck on its proximal surface 112s. With the locking mechanism 118 in the unlocked position, the outer shaft 108 extends through the enlarged diameter portion 120b and the strike cap 112 is located proximal to the keyhole 120. The diameter of the enlarged diameter portion 120b is greater than the diameter of the strike cap 112 at least at the distal end of the strike cap 112. The strike cap 112 thus can move distally into the keyhole 120, thereby allowing the outer shaft 108 to move distally by the strike cap 112 being struck on its proximal surface 112s. The diameter of the enlarged diameter portion 120b is less than a diameter of a head of the strike cap 112 that includes the proximal surface 112s, thereby preventing the strike cap 112 from fully passing into the keyhole 120 because a distal surface of the strike cap 112 will abut the locking mechanism 118 around the keyhole 120. FIG. 7 shows the locking mechanism 118 in the unlocked position after the strike cap 112 has been struck with the distal surface of the strike cap 112 abutting the locking mechanism 118 around the keyhole 120.

The locking mechanism 118 in this illustrated embodiment is not releasable from the inserter tool 100. In other embodiments, a locking mechanism is releasable from the inserter tool 100. Various embodiments of locking mechanisms are further described, for example, in previously mentioned U.S. Pat. Pub. No. 2021/0338223 entitled "Knotless Anchor Insertion" published Nov. 4, 2021.

As shown in FIG. 4, the inner shaft's distal end defines a fork. The inner shaft 110 includes a pair of opposed distal arms 122 that define a suture retention channel 124 therebetween. The suture retention channel 124 has an open distal end and a closed proximal end. The suture retention channel 124 is configured to releasably retain a suture therein with the suture extending through the slots 104 of the anchor 102, as discussed further below. As also shown in FIG. 4, with the anchor 102 coupled to the inserter 100 and with the inserter 100 in the initial configuration, the suture retention channel 124 is located within the anchor 102, e.g., within the inner lumen 102i of the anchor 102, and is located distal to the outer shaft 108 but is not located distal to the anchor 102.

The suture retention channel 124 may allow for more sutures and/or larger diameter suture(s) to be coupled to the inserter 100 than with other types of inserter tools since the suture(s) do not need to be folded over to be inserted into an aperture, eyelet, or other opening to be coupled to the inserter tool or to the anchor.

The suture retention channel 124 has a substantially constant diameter in this illustrated embodiment but can have different diameters in different portions, e.g., a proximal portion of the suture retention channel 124 having a greater diameter than a distal portion of the suture retention channel, a distal portion of the suture retention channel 124 having a greater diameter than a proximal portion of the suture retention channel, or other different diameters. A person skilled in the art will appreciate that values, such as diameter values, may not be precisely the same but nevertheless considered to be substantially the same for any of one or more reasons, such as manufacturing tolerances or sensitivity of measurement equipment.

Figure 8:
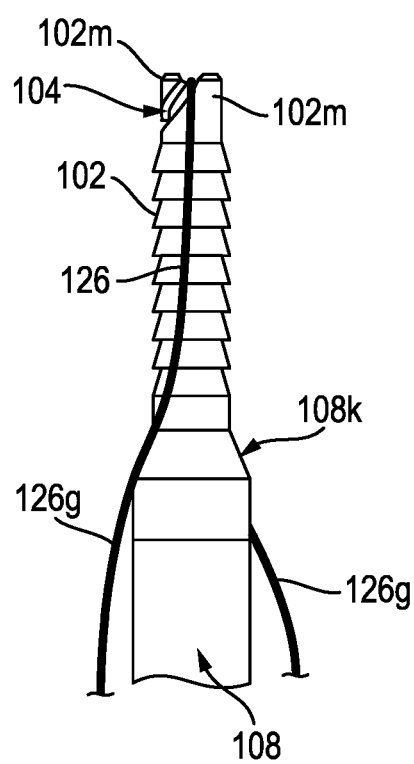
FIG. 8 is a side view of the anchor and a distal portion of the inserter tool of FIG. 1 having a suture releasably coupled thereto with an inner shaft of the inserter tool in a first position.
Figure 9:
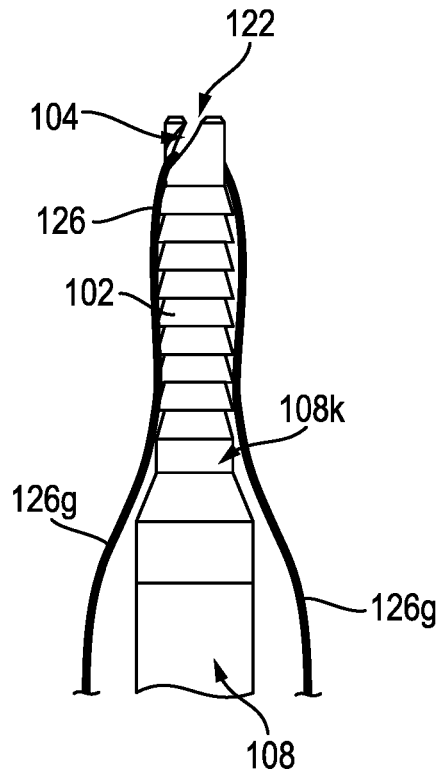
FIG. 9 is a side view of the anchor, the suture, and the distal portion of the inserter tool of FIG. 8 with the inner shaft of the inserter tool in a second position.

FIGS. 8 and 9 illustrate one embodiment of coupling a suture 126 to the inserter tool 100 and the anchor 102 by seating the suture 126 in the inner shaft's suture retention channel 124 and in the anchor's slots 104. In an exemplary embodiment, the suture 126 is coupled to the inserter tool 100 and the anchor 102 by a user, which may allow the user to select a particular size and type of suture as appropriate for the surgical procedure being performed and to select whether to use one or more sutures. FIGS. 8 and 9 show coupling a single suture 126 to the inserter tool 100 and the anchor 102.

With the inserter 100 in the initial configuration, as shown in FIGS. 4 and 8, each of the distal arms 122 of the inner shaft 110 is aligned with one of the distal arms 102m of the anchor 102, and the inner shaft's distal arms 122 are misaligned from the anchor's slots 104. With the inner shaft 110 and the anchor 102 in this relative position to one another, a distal end of each of the slots 104 is open and unobstructed. The suture 126 can thus be slid or otherwise moved into the slots 104 and be positioned within the suture retention channel 124, as shown in FIG. 8. Legs 126g of the suture 126 extend outside of the anchor 102 and the outer shaft 108 with an intermediate portion of the suture 126 between the legs 126g being at a distal portion of the slots 104 and a distal portion of the suture retention channel 124. The suture 126 extends along the anchor's distal end so as to loop around the anchor's distal end. The suture 126 can be slid into the slots 104 directly, or the suture 126 can first be seated in the suture retention channel 124 with the inner shaft 110 extending distally beyond the anchor 102 and then the outer shaft 108 and the anchor 102 moved distally relative to the inner shaft 110 to move the suture 126 into the slots 104.

Figure 10:
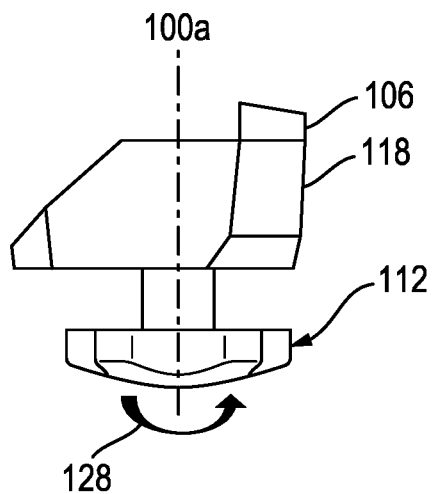
FIG. 10 is a side view of a proximal portion of the inserter tool of FIG. 1.

With the intermediate portion of the suture 126 being in the slots 104 and the suture retention channel 124, the outer shaft 108 and the anchor 102 are rotated about the longitudinal axis 100a relative to the inner shaft 110. The knob 112 is configured to be rotated in first direction, as shown by arrow 128 in FIG. 10, to rotate the outer shaft 108 and the anchor 102 relative to the inner shaft 110. The anchor 102 being releasably mated to the outer shaft 108 allows the anchor 102 to rotate as a unit with the outer shaft 108. The knob 112, the outer shaft 108, and the anchor 102 are rotated counterclockwise in this illustrated embodiment but could instead be rotated clockwise. The outer shaft 108 and the anchor 102 are rotated about 90°, e.g., by rotating the knob 112 about 90°, which allows the inner shaft's arms 122 to be in a maximally obstructive position relative to the anchor's slots 104. A person skilled in the art will appreciate that a value may not be precisely at a value but nevertheless considered to be at about that value for any of one or more reasons, such as manufacturing tolerances or sensitivity of measurement equipment.

The inserter tool 100 can include an indicator configured to indicate a rotational position of the knob 112 and thus indicate a rotational position of the anchor 102 and the outer shaft 108 relative to the inner shaft 110. The indicator is configured to be located outside of a patient's body when the anchor 102 is located within the patient's body, thereby allowing the rotational position of the anchor 102 and the outer shaft 108 to be easily determined by a user even if the anchor 102 and/or the outer shaft 108 are not currently visible within the patient's body. The indicator can have a variety of configurations. For example, the indicator can include a first marking on the knob 112 and a second marking on the handle 106 and/or the locking mechanism 118. The first and second markings can have any of a variety of configurations, such as dots, lines, numbers, letters, arrows, or other mark. The first and second markings are misaligned with the inserter tool 100 in the initial configuration. As the knob 112 rotates, the first and second markings move toward alignment. Alignment of the first and second markings indicates that the knob 112, and thus the anchor 102 and the outer shaft 108, have been rotated 90°. For another example, the indicator can include a stop surface of the knob 112 configured to abut a corresponding stop surface of the handle 106 and/or the locking mechanism 118. When the stop surfaces abut one another, the knob 112 cannot be further rotated in the first direction, thereby indicating that the inner shaft 110 is in a proper rotational position relative to the anchor 102 to lock the suture 126 in position.

The rotation of the anchor 102 relative to the inner shaft 110 causes the inner shaft's distal arms 122 to become misaligned from the anchor's distal arms 102m and to become aligned with the anchor's slots 104, as shown in FIG. 9. The rotation of the anchor 102 causes the inner shaft's distal arms 122 to push the suture 126 proximally within the slots 104 and the suture retention channel 124 such that the intermediate portion of the suture 126 is located more proximal than before the anchor's rotation, as shown in FIG. 8 (pre-rotation) and FIG. 9 (post-rotation). The distal arms 122 of the inner shaft 110 lock the suture 126 in the slots 104 by effectively obstructing the slots 104. The inner shaft 110 and the anchor 102 can thereby form a temporary enclosure for a suture seated in the suture retention channel 124 and extending through the slots 104. The locked suture 126 is in a fixed position relative to the anchor 102, the inner shaft 110, and the outer shaft 108.

Alternatively, instead of the anchor 102 and the outer shaft 108 being rotated relative to the inner shaft 110, the inner shaft 110 can be rotated relative to the anchor 102 and the outer shaft 108.

FIGS. 11-14 illustrate one embodiment of a method of inserting a suture anchor into bone using an inserter tool. The method is described with respect to the inserter tool 100 and the anchor 102 of FIGS. 1-10 but can be similarly performed with other inserter tools and anchors.

Figure 11:
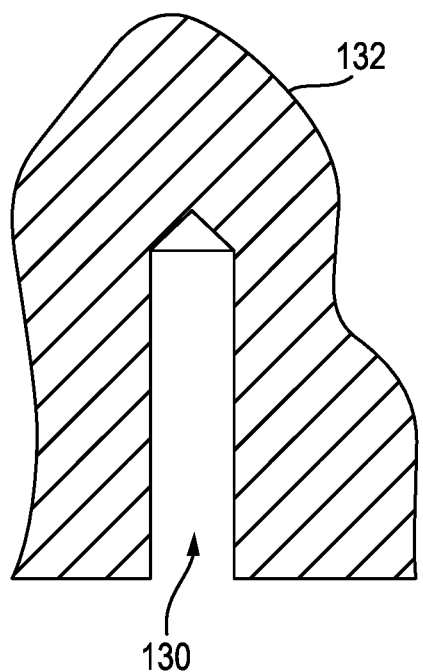
FIG. 11 is a side schematic view of a bone having a hole formed therein.

With the suture 126 coupled to the inserter 100 and the anchor 102, the inserter 100 is used to insert the suture 126 and the anchor 102 into a hole 130 in bone 132. In an exemplary embodiment of using the inserter 100 to insert the suture 126 and the anchor 102 into the bone hole 130, a drill or other bone removal tool is inserted into a patient's body, as will be appreciated by a person skilled in the art, to form the bone hole 130 in bone 132 as shown in FIG. 11. The drill or other bone removal tool can be advanced into the patient's body, and then removed from the patient's body, through a cannula positioned within an opening, e.g., an incision, formed in the patient's skin, as will also be appreciated by a person skilled in the art. The cannula can then serve as a guide for the inserter's distal advancement toward the bone hole 130.

Before or after the bone hole 130 is formed, the suture 126 is coupled and locked to the anchor 102 as discussed above and as shown in FIG. 9. With the suture 126 coupled and locked to the anchor 102 so as to be fixed in position relative to the anchor 102, the inner shaft 110, and the outer shaft 108, the inserter 100 is advanced distally into the body of the patient and positioned relative to the bone hole 130. The suture 126 and the anchor 102 can thus be ziplined from outside the patient's body and into position relative to the bone hole 130 while being in a predictable, fixed position relative to one another without risk of the suture 126 falling out of the anchor 102. The suture 126 thus need not be reloaded intraoperatively or reloaded outside the patient's body with the inserter 100 first being removed from the patient's body to allow for suture reloading.

Figure 12:
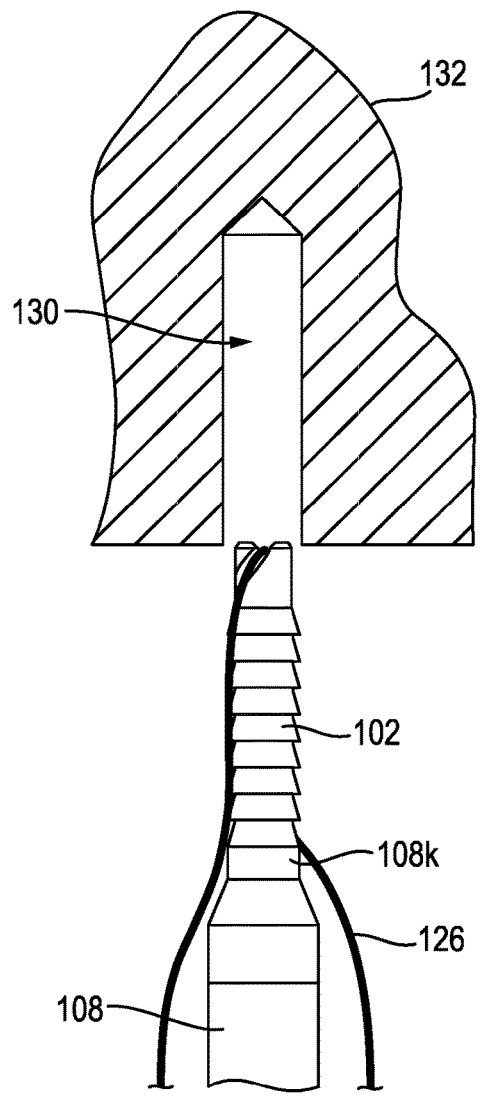
FIG. 12 is a side view of the inserter tool and anchor of FIG. 1 positioned outside and adjacent to the bone hole of FIG. 11.
Figure 13:
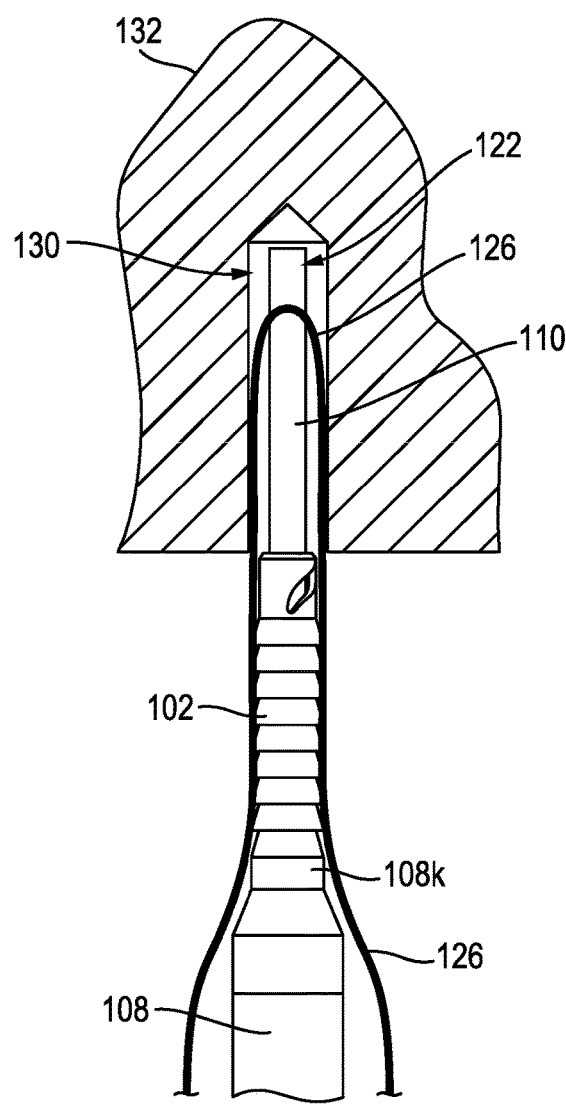
FIG. 13 is a side view of the inserter tool and anchor of FIG. 12 with and an inner shaft of the inserter tool and a suture advanced into the bone hole.

With the anchor 102 and the inserter 100 positioned relative to the bone hole 130, the suture 126 is unlocked by the anchor 102 and the outer shaft 108 being rotated relative to the inner shaft 110 opposite to that discussed above to lock the suture 126 in position. The inner shaft 110 is thus changed from its position of FIG. 9 to its position of FIG. 8 by the knob 112 being rotated in a second, opposite direction, e.g., clockwise, to rotate the anchor 102 and the outer shaft 108 relative to the inner shaft 110. The rotation of the anchor 102 relative to the inner shaft 110 in the second direction causes the inner shaft's distal arms 122 to again become aligned with the anchor's distal arms 102m and to again become misaligned from the anchor's slots 104. FIG. 12 shows the inserter 100 and the anchor 102 positioned relative to the bone hole 130 and the suture 126 in the unlocked position after the rotation of the inner shaft 110 in the second direction. Continued rotation of the knob 112 causes the outer shaft 108 and the anchor 102 to move proximally relative to the inner shaft 110 such that the inner shaft 110 extends distally beyond the anchor 102 and the outer shaft 108. The anchor 102 being releasably mated to the outer shaft 108 allows the anchor 102 to move as a unit with the outer shaft 108. With downward (distal) axial pressure applied to the anchor 108 against a mouth of the bone hole 130 as the knob 112 is rotated, the inner shaft 110 will be able to extend into the bone hole 130, as shown in FIG. 13. (The inner shaft 110 is shown in longitudinal cross-section in FIG. 13 to better show the suture's position relative to the inner shaft 110 and the bone 132.)

The distal extension of the inner shaft 110 beyond the anchor 102 causes the suture 126 to correspondingly be pushed distally out of the slots 104 and into the bone hole 130. As the inner shaft 110 moves into the bone hole 130, the suture 126 will abut the proximal end of the fork defined by the inner shaft's distal arms 122 such that continued distal advancement of the inner shaft 110 will cause the suture 126 to also move distally and into the bone hole 130. The suture 126 is thus positioned in the bone hole 130 before the anchor 102 is secured in the bone hole 130. In other words, the suture 126 seated in the inner shaft's suture retention channel 124 and the anchor's slots 104 can be positioned in the bone hole 130 distal to the anchor 102, thereby allowing the anchor 102 to be advanced distally into the bone hole 130 with the suture 126 already positioned in the bone hole 130. A bottom surface of the bone hole 130 can act as a stop surface that stops the inner shaft 110 relative to the bone 132. An interior of the bone hole 130 cannot be visualized with the inserter 100 positioned in the bone hole 130, so a surface of the bone hole 130 acting as a stop can help ensure that the inserter 100 has been advanced as far as distally possible within the bone hole 130, which may help ensure that the anchor 102 is secured in the bone hole 130 with the anchor's proximal end flush or sub-flush with a proximal end of the bone hole 130.

With the suture 126 positioned in the bone hole 130 and a distal portion of the inner shaft 110 positioned in the bone hole 130, and prior to distal advancement of the anchor 102 relative to the inner shaft 110, the suture 126 can be tensioned as desired. The suture 126 can be slid relative to the anchor 102 (and to the inner shaft 110 and the outer shaft 108), e.g., by pulling the legs 126g of the suture 126, to allow the suture 126 to be desirably tensioned and thus for soft tissue tied or otherwise attached to the suture 126 to be desirably positioned relative to the bone 132 in which the anchor 102 will be secured. As shown in FIG. 13, the suture 126 positioned in the bone hole 130 has a U-shape. The suture 126 having the U-shape before anchor 102 insertion into the bone hole 130 allows for the suture 126, after anchor 102 insertion into the bone hole 130, to have each of the suture's two legs 126g extending longitudinally along opposed sides of the anchor 102, and an intermediate portion of the suture 126 that connects the legs 126 extending along the anchor's distal end so as to loop around the anchor's distal tip end.

With the suture 126 positioned in the bone hole 130 and a distal portion of the inner shaft 110 positioned in the bone hole 130, and with the suture 126 at a desired tension, the locking mechanism 118 is moved from the locked position to the unlocked position. The outer shaft 108 is now free to move distally relative to the inner shaft 110 in response to a strike on the strike cap 112.

With the suture 126 positioned in the bone hole 130 and the distal portion of the inner shaft 110 positioned in the bone hole 130, and with the suture 126 at a desired tension and the locking mechanism 118 in the unlocked position, the anchor 102 is advanced distally into the bone hole 130 by longitudinally translating the anchor 102 relative to the inner shaft 110 in a distal direction. In other words, the anchor 102 is pushed axially along the longitudinal axis 100a of the inserter 100. The strike cap 112 is hit with a mallet, hammer, or other tool to cause the outer tube 108 to move distally relative to the inner shaft 110, which causes the anchor 102 to move distally relative to the inner shaft 110 and advance distally into the bone hole 130. The strike cap 112 may be hit one or more times to fully advance the anchor 102 into the bone hole 130. The anchor 102 in the bone hole 130 traps the suture 126, e.g., the legs 126g thereof, between the exterior surface of the anchor 102 and an interior bone surface defining the bone hole 130.

Figure 14:
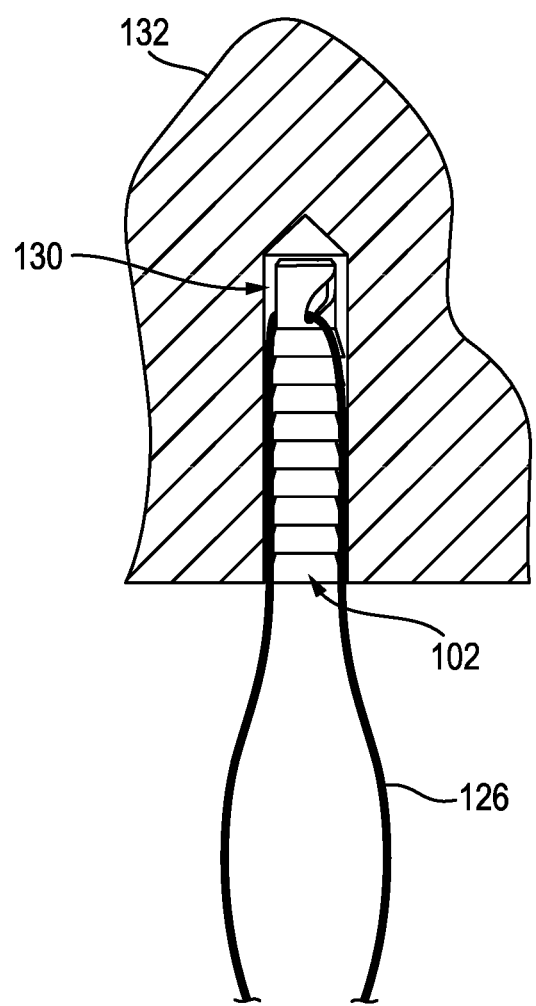
FIG. 14 is a side view of the anchor and the suture of FIG. 13 secured in the bone hole.

After the anchor 102 has been inserted into the bone hole 130, the inserter 100, including the outer and inner shafts 108, 110, is longitudinally translated in a proximal direction, e.g., pulled axially along the longitudinal axis 100a of the inserter 100, to be removed from the patient's body with the anchor 102 and the suture 126 remaining in the bone 132. The proximal movement of the outer shaft 108 releases the mating element of the anchor 102 and the mating feature of the outer shaft 108 since the anchor 102 has been secured in the bone 132 and can thus stay within the bone hole 130 as the outer shaft 108 is moved proximally. FIG. 14 shows the anchor 102 having been distally advanced and positioned in the bone hole 130 after removal of the inserter 100. The suture 126 automatically exits the inner shaft's suture retention channel 124 in response to the proximal pulling of the inner shaft 110 out of the bone hole 130. Tails of the suture 126 can be trimmed as desired.

Figure 15:
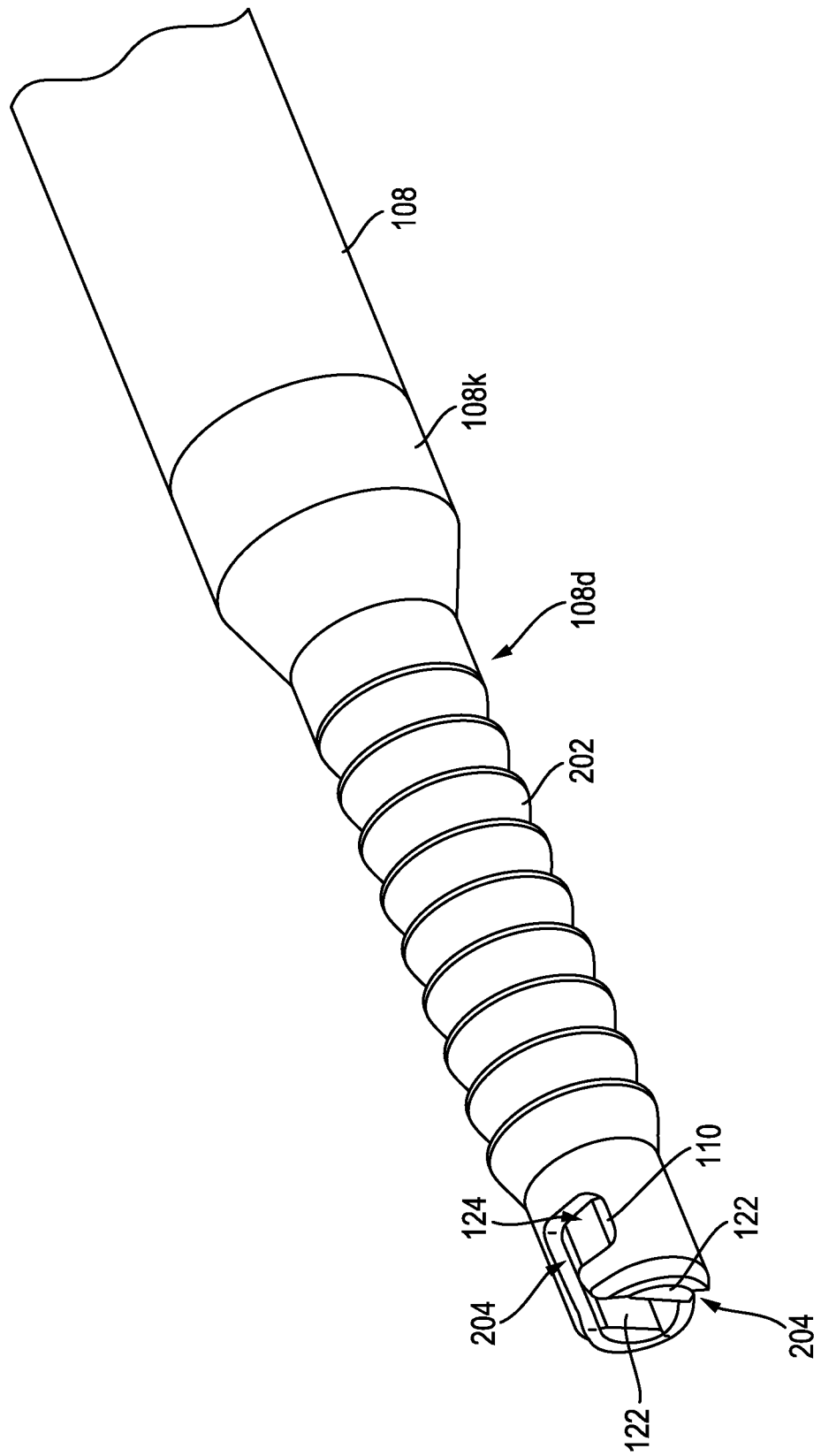
FIG. 15 is a perspective view of a distal portion the inserter tool of FIG. 1 and another embodiment of a suture anchor releasably coupled to the inserter tool.

FIG. 15 illustrates another embodiment of an anchor 202. The anchor 202 is shown in FIG. 15 coupled to the inserter tool 100, but the anchor 202 can be similarly used with other inserter tools. The inserter tool 100 is shown in the initial configuration in FIG. 15, similar to the inserter tool's position in FIG. 4. The anchor 202 is configured and used similar to the anchor 102 of FIGS. 1-4, 8, 9, and 12-14 except that a pair of opposed slots 204 of the anchor 202 has a different configuration than the pair of opposed slots 104 of the anchor 102. In this illustrated embodiment, each slot 204 has an L-shape. Each slot 204 has a vertical arm with an open distal end that extends proximally from an open distal end of the anchor 202, and has a horizontal arm that extends laterally from a proximal end of the vertical arm. The vertical arms are substantially parallel to the inserter's longitudinal axis 100a and thus to the anchor's longitudinal axis coaxial therewith, and the horizontal arms are transverse (substantially perpendicular in this illustrated embodiment) to the inserter's longitudinal axis 100a and the anchor's longitudinal axis. A person skilled in the art will appreciate that axes may not be precisely parallel or precisely perpendicular but nevertheless considered to be substantially parallel or substantially perpendicular for any of one or more reasons, such as manufacturing tolerances or sensitivity of measurement equipment. The horizontal arm is wider than the vertical arm, which may help lock a suture within the slots 204, e.g., within the horizontal arms thereof, by providing ample room for the suture to be seated and captured.

Figure 16:
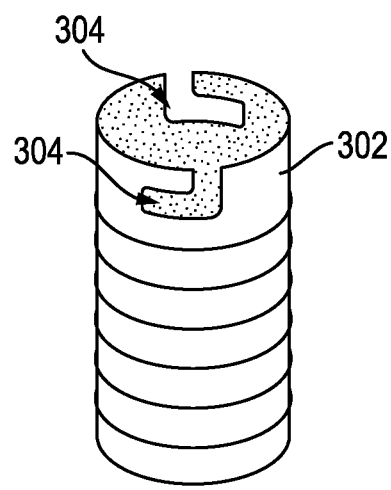
FIG. 16 is a perspective view of yet another embodiment of a suture anchor.

FIG. 16 illustrates another embodiment of an anchor 302. The anchor 302 is configured and used similar to the anchor 102 of FIGS. 1-4, 8, 9, and 12-14, including use thereof with the inserter tool 100 or other inserter tool, except that a pair of opposed slots 304 of the anchor 302 has a different configuration than the pair of opposed slots 104 of the anchor 102. In this illustrated embodiment, each slot 304 has an L-shape, similar to the slots 204 of FIG. 15. However, in this illustrated embodiments, each slot's vertical arm and horizontal arm have a same width.

Figure 17:
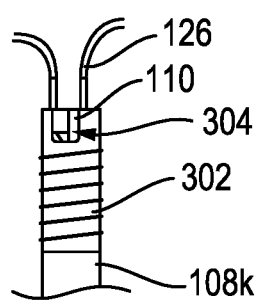
FIG. 17 is a side view of the anchor of FIG. 16 releasably coupled to the inserter tool of FIG. 1 and the suture of FIG. 8.
Figure 18:
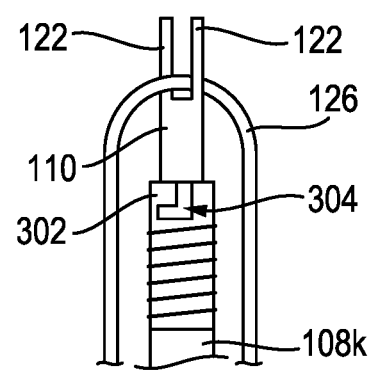
FIG. 18 is a side view of the anchor and the suture of FIG. 17 with the suture and the inner shaft of the inserter tool advanced distally relative to the anchor.

FIG. 17 illustrates the anchor 302 and the inner shaft 110 with the suture 126 locked relative thereto. The suture 126 is seated in the suture retention channel 124 and extends through the slots 304 with the suture 126 being positioned in the horizontal arms of the slots 304. The arms 122 of the inner shaft 110 are obstructing the slots 304. FIG. 18 illustrates the anchor 302, the inner shaft 110, and the suture 126 of FIG. 17 after the anchor 302 has been rotated to unlock the suture 126 and has been moved proximally relative to the anchor 302 with the outer shaft 108 to push the suture 126 out of the slots 304. The anchor 302 is shown with the inserter tool 100 of FIGS. 1-3 in FIGS. 17 and 18 but can be similarly used with other inserter tools. Also, the anchor 302 is shown with the suture 126 of FIGS. 12-14 in FIGS. 17 and 18 but can be similarly used with other sutures.

Figure 19:
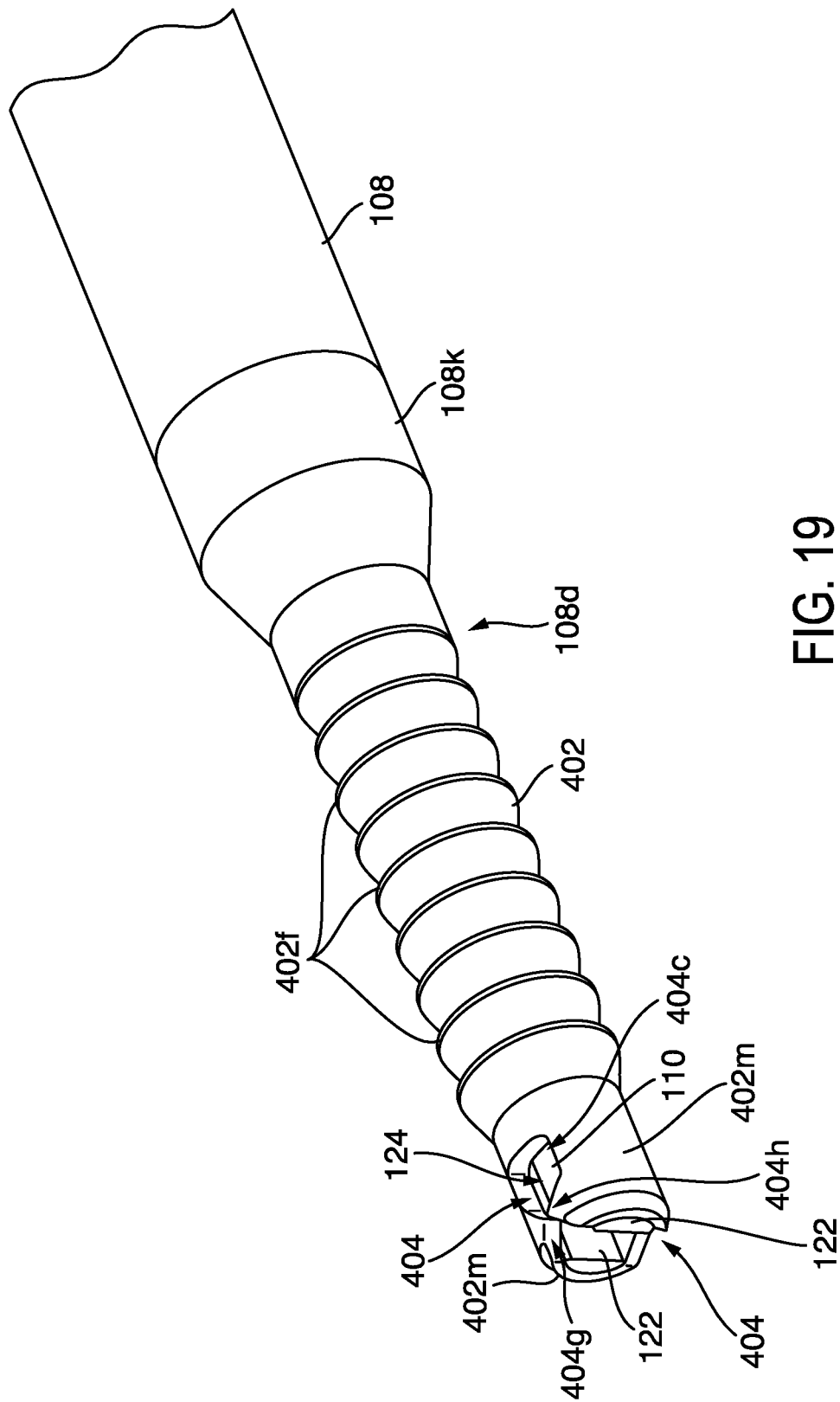
FIG. 19 is a perspective view of a distal portion the inserter tool of FIG. 1 and still another embodiment of a suture anchor releasably coupled to the inserter tool.

FIG. 19 illustrates another embodiment of an anchor 402. The anchor 402 is shown in FIG. 19 coupled to the inserter tool 100, but the anchor 402 can be similarly used wither other inserter tools. The inserter tool 100 is shown in the initial configuration in FIG. 19, similar to the inserter tool's position in FIG. 4. The anchor 402 is configured and used similar to the anchor 102 of FIGS. 1-4, 8, 9, and 12-14 except that a pair of opposed slots 404 of the anchor 402 has a different configuration than the pair of opposed slots 104 of the anchor 102. In this illustrated embodiment, each slot 404 includes a notch. The notches are formed in a distal portion of the anchor 402 that does not include any bone-engaging features 402*f* and are defined by opposed distal arms 402*m* of the anchor 402.

Each slot 404 includes a distal suture guide groove 404*g*, a proximal cut-out 404*c*, and a channel 404*h* connecting the distal suture guide groove 404*g* and the proximal cut-out 404*c*. Each distal suture guide groove 404*g* is defined by opposed wings at a distal end of the anchor's distal arms 402*m*. The wings each extend radially outward so as to define a V-shape. Each suture guide groove 404*g* is thus V-shaped, with the tip of the "V" pointing proximally. Each cut-out 404*c* is located distal to its corresponding suture guide groove 404*g*. The cut-outs 404*c* in this illustrated embodiment each have a pentagon shape defined by a square and a triangle, with the triangle being distal to the square and pointing distally, but the cut-outs 404*c* can have other shapes, e.g., teardrop-shaped, diamond-shaped, etc.

In general, the slots 404 are configured to receive a suture therein. The suture can move distally through the suture guide groove 404*g* to enter the channel 404*h* and then to enter the cut-outs 404*c*. The suture guide groove 404*g* and the cut-outs 404*c* each have a width that is greater than a width of the channel 404*h*, which may help retain a suture in the cut-outs 404*c* by discouraging, if not preventing, the suture from moving distally out of the cut-outs 404*c* before a desired time of suture decoupling from the anchor 402, e.g., by pushing the suture distally with an inner shaft of an inserter tool.

The suture guide groove 404*g* is configured to receive a suture therein that engages inner surfaces of the arms' wings. The suture can then be slid proximally along the wing's inner surfaces to guide the suture to an apex of each suture guide groove 404*g*, e.g., to the point of the groove's V-shape. The suture can be slid along any of the wings' inner surface. The suture continues to be slid proximally to enter the longitudinal channel 404*h*. Thus, movement of the suture in the suture guide groove 404*g* in a proximal direction causes the suture to enter the channel 404*h*. Continued movement of the suture in a proximal direction within the channel 404*h* causes the suture to enter the cut-outs 404*c*. A closed proximal end of the cut-outs 404*c* acts as a stop surface for the suture in the cut-outs 404*c*, although in some embodiments the suture may be positioned in the cut-outs 404*c* but not abut one or both stop surfaces. As discussed further below, the suture received in and extending through the cut-outs 404*c* can be pushed distally out of the cut-outs 404*c*, then distally through the channel 404*h*, and then distally out of the suture guide groove 404*g*. As discussed below, the distal arms 402*m* of the anchor 402 can be configured to splay radially outward as the suture passes into and through the channel 404*h* and can be configured to splay radially inward after the suture exits the channel 404*h* to enter the cut-outs 404*c* or the suture guide grooves 404*g*.

The distal arms 402*m* of the anchor 402 are configured to spring back and forth relative to one another, similar to tweezer arms. The movement of the distal arms 402*m* relative to one another is configured to change the width of the channel 404*h* to facilitate seating of a suture in the cut-outs 404*c* and removal of the suture from the cut-outs 404*c*. FIG. 19 shows the arms 402*m* in a resting configuration in which the width of the channel 404*h* is at a minimum. The distal arms 402*m* are configured to move from the resting configuration to an expanded configuration in which the arms 402*m* are moved radially outward such that a width of the channel 404*h* increases. The expanded width of the channel 404*h* provides more space for the suture to enter into the cut-outs 404*c* and for the suture to exit from the cut-out 404*c*. The arms 402*m* are biased to the resting configuration such that the arms 402*m* are configured to dynamically move from the resting configuration to the expanded configuration in response to the suture being advanced proximally into or distally out of the cut-outs 404*c*, such that the arms 402*m* are configured to dynamically move from the expanded configuration to the resting configuration in response to the suture being advanced proximally out of the suture guide groove 404*g* and into the cut-outs 404*c*, and such that arms 402*m* are configured to dynamically move from the resting configuration to the expanded configuration in response to the suture being advanced distally out of the cut-outs 404*c* and into the suture guide groove 404*g*.

Alternatively, the distal arms 402*m* of the anchor 402 can not be configured to spring back and forth relative to one another. In such embodiments, a suture's compressibility can be sufficient to allow the suture to move through the channel 404*h*.

Figure 20:
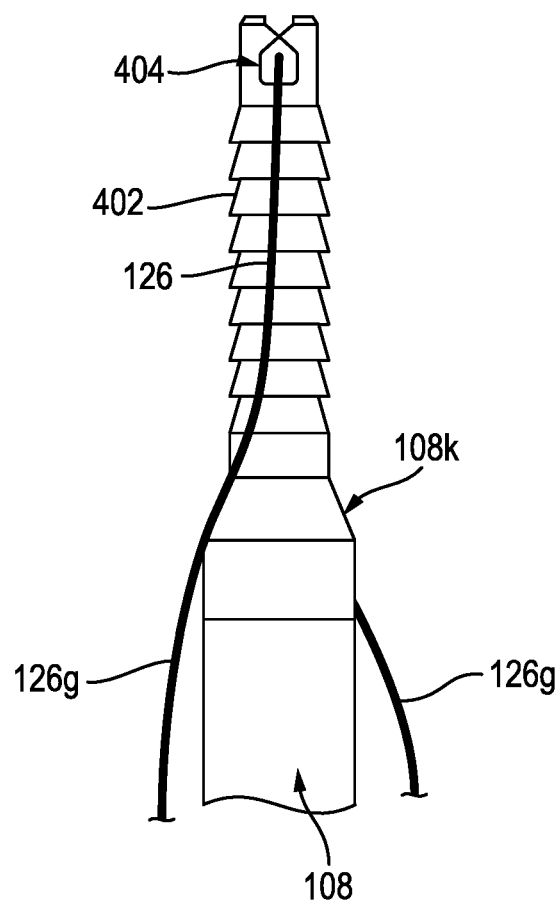
FIG. 20 is a side view of the anchor and a distal portion of the inserter tool of FIG. 19 having the suture of FIG. 8 releasably coupled thereto with the inner shaft of the inserter tool in a first position.

FIG. 20 illustrates the suture 126 seated in the slots 404. The anchor 402 is shown in FIG. 20 coupled to the inserter tool 100 and the suture 126, but the anchor 402 can be similarly used wither other inserter tools and sutures. The inserter tool 100 in FIG. 20 is in the initial configuration with each of the distal arms 122 of the inner shaft 110 aligned with one of the distal arms 402*m* of the anchor 402, and the inner shaft's distal arms 122 misaligned from the anchor's slots 404.

Figure 21:
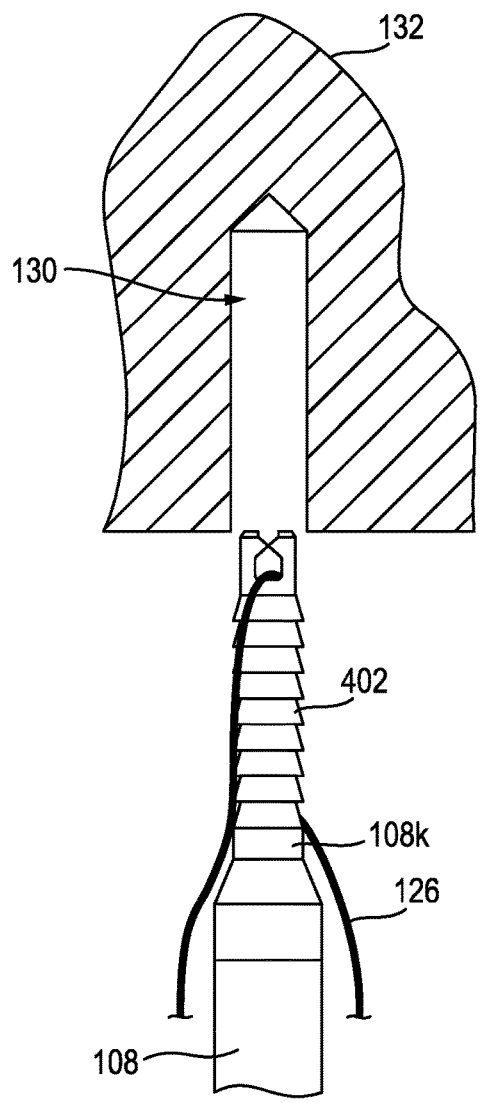
FIG. 21 is a side view of the inserter tool, suture, and anchor of FIG. 20 positioned outside and adjacent to the bone hole of FIG. 11.
Figure 22:
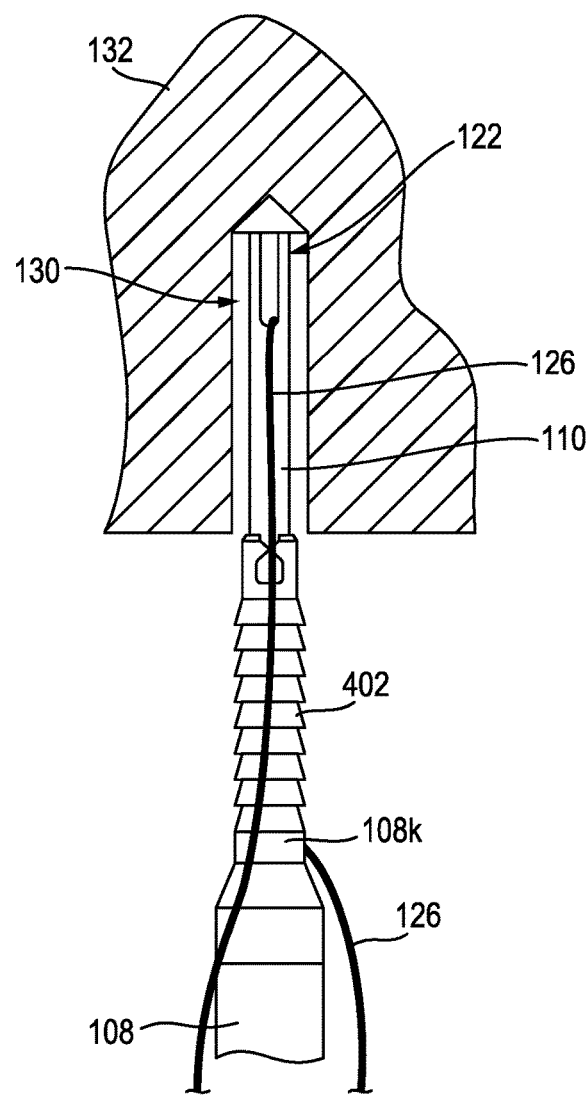
FIG. 22 is a side view of the anchor and the suture of FIG. 21 with the suture and the inner shaft of the inserter tool advanced into the bone hole.
Figure 23:
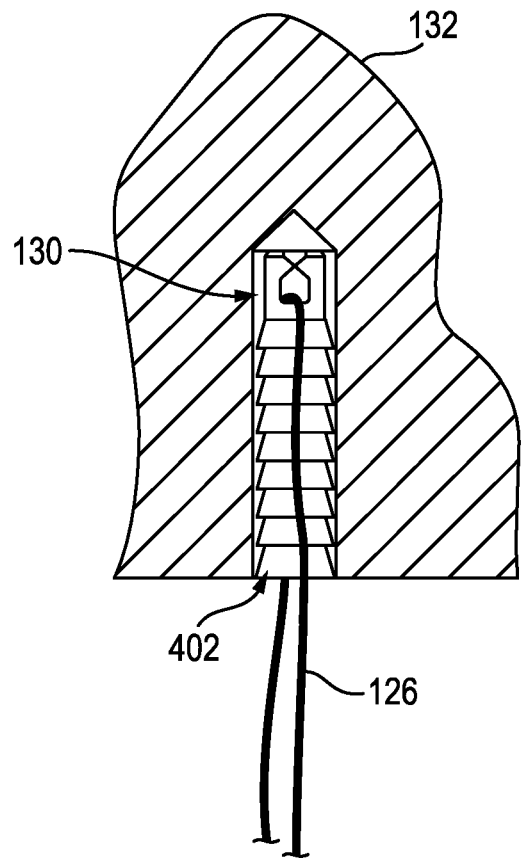
FIG. 23 is a side view of the anchor and the suture of FIG. 22 secured in the bone hole.

FIGS. 21-23 illustrate one embodiment of a method of inserting the suture anchor 402 into bone 132 using the inserter tool 100. The method is described with respect to the inserter tool 100 of FIGS. 1-10, the bone 132 and bone hole 130 of FIGS. 11-14, the suture 126 of FIGS. 12-14, and the anchor 402 of FIG. 18 but can be similarly performed with other inserter tools, bones, bone holes, sutures, and anchors.

With the suture 126 coupled to the inserter 100 and the anchor 402, the inserter 100 is used to insert the suture 126 and the anchor 402 into the bone hole 130, which can be formed as discussed above. Before or after the bone hole 130 is formed, the suture 126 is coupled to the anchor 402 as shown in FIG. 20. The suture 126 is then locked to the anchor 402 similar to that discussed above regarding the anchor 102 and the suture 126, with the outer shaft 108 and the anchor 402 being rotated to align the inner shaft's arms 122 with the slots 404 of the anchor 402.

With the suture 126 coupled and locked to the anchor 402 so as to be fixed in position relative to the anchor 402, the inner shaft 110, and the outer shaft 108, the inserter 100 is advanced distally into the body of the patient and positioned relative to the bone hole 130. The suture 126 and the anchor 402 can thus be ziplined from outside the patient's body and into position relative to the bone hole 130 while being in a predictable, fixed position relative to one another without risk of the suture 126 falling out of the anchor 402.

With the anchor 402 and the inserter 100 positioned relative to the bone hole 130, the suture 126 is unlocked by the anchor 402 being rotated relative to the inner shaft 110 opposite to that discussed above to lock the suture 126 in position, e.g., by rotating the knob 112 of the inserter 100 to rotate the anchor 402 and the outer shaft 108. The rotation of the anchor 402 relative to the inner shaft 110 in the second direction causes the inner shaft's distal arms 122 to again become aligned with the anchor's distal arms 402m and to again become misaligned from the anchor's slots 404. FIG. 21 shows the inserter 100 and the anchor 402 positioned relative to the bone hole 130 and the suture 126 in the unlocked position after the rotation of the anchor 402 in the second direction. The inner shaft 110 is then positioned in the bone hole 130, as shown in FIG. 22, similar to that discussed above regarding the anchor 102.

The inner shaft 110 moving into the bone hole 130 causes the suture 126 to correspondingly be pushed distally out of the slots 404 to be pushed into the bone hole 130. As the inner shaft 110 advances into the bone hole 130, the suture 126 will abut the proximal end of the fork defined by the inner shaft's distal arms 122 such that continued distal advancement of the inner shaft 110 will cause the suture 126 to also move distally and into the bone hole 130. The suture 126 is thus positioned in the bone hole 130 before the anchor 402 is secured in the bone hole 130. In other words, the suture 126 seated in the inner shaft's suture retention channel 124 and the anchor's slots 404 can be positioned in the bone hole 130 distal to the anchor 402, thereby allowing the anchor 402 to be advanced distally into the bone hole 130 with the suture 126 already positioned in the bone hole 130. A bottom surface of the bone hole 130 can act as a stop surface that stops the inner shaft 110, as discussed above.

With the suture 126 positioned in the bone hole 130 and a distal portion of the inner shaft 110 positioned in the bone hole 130, and prior to distal advancement of the anchor 402 relative to the inner shaft 110, the suture 126 can be tensioned as desired, as discussed above. The suture 126 positioned in the bone hole 130 in FIG. 22 has a U-shape, as discussed above.

With the suture 126 positioned in the bone hole 130 and a distal portion of the inner shaft 110 positioned in the bone hole 130, and with the suture 126 at a desired tension, the locking mechanism 118 is moved from the locked position to the unlocked position. The outer shaft 108 is now free to move relative to the inner shaft 110 in response to a strike on the strike cap 112.

With the suture 126 positioned in the bone hole 130 and the distal portion of the inner shaft 110 positioned in the bone hole 130, and with the suture 126 at a desired tension and the locking mechanism 118 in the unlocked position, the anchor 402 is advanced distally into the bone hole 130 by longitudinally translating the anchor 402 relative to the inner shaft 110 in a distal direction. In other words, the anchor 402 is pushed axially along the longitudinal axis 100a of the inserter 100. The strike cap 112 is hit with a mallet, hammer, or other tool to cause the outer tube 108 to move distally relative to the inner shaft 110, which causes the anchor 402 to move distally relative to the inner shaft 110 and advance distally into the bone hole 130. The strike cap 112 may be hit one or more times to fully advance the anchor 402 into the bone hole 130. The anchor 402 in the bone hole 130 traps the suture 126, e.g., the legs 126g thereof, between the exterior surface of the anchor 402 and an interior bone surface defining the bone hole 130.

After the anchor 402 has been inserted into the bone hole 130, the inserter 100, including the outer and inner shafts 108, 110, is longitudinally translated in a proximal direction, e.g., pulled axially along the longitudinal axis 100a of the inserter 100, to be removed from the patient's body with the anchor 402 and the suture 126 remaining in the bone 132. FIG. 23 shows the anchor 402 having been distally advanced and positioned in the bone hole 130 after removal of the inserter 100. The suture 126 automatically exits the inner shaft's suture retention channel 124 in response to the proximal pulling of the inner shaft 110 out of the bone hole 130. Tails of the suture 126 can be trimmed as desired.

In some embodiments, an outer shaft of an inserter tool and an anchor are not rotated to form a temporary enclosure for a suture in cooperation with the anchor that is releasably coupled to the inserter tool. In such embodiments, an inner shaft of the inserter tool is configured to move axially along coaxial longitudinal axes of the inserter tool and the anchor releasably coupled to the inserter tool to facilitate suture capture prior to securing the suture in bone with the anchor. In such embodiments, the inserter tool's strike cap need not be configured to rotate. Various embodiments of non-rotating strike caps are described in previously mentioned U.S. Pat. Pub. No. 2021/0338223 entitled "Knotless Anchor Insertion" published Nov. 4, 2021.

Figure 24:
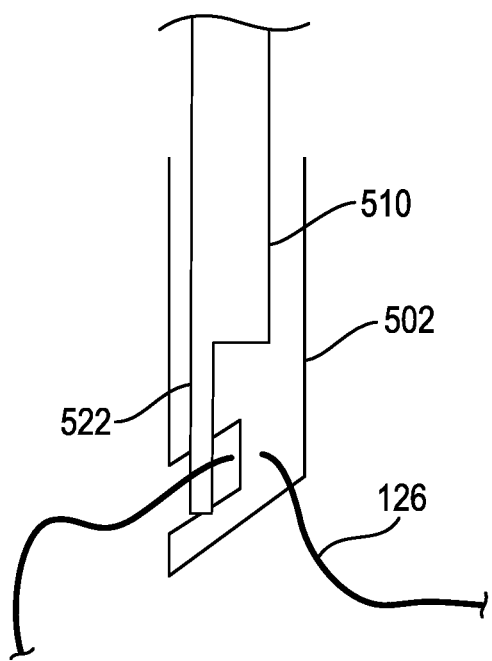
FIG. 24 is a side partially transparent view of another embodiment of an inner shaft of an inserter tool and another embodiment of a suture anchor releasably coupled to the inserter tool.

FIG. 24 illustrates another embodiment of an inserter tool and another embodiment of an anchor 502. The inserter tool of FIG. 24 is configured and used similar to the inserter tool 100 of FIGS. 1-3 except that an inner shaft 510 of the inserter tool is configured to move axially along coaxial longitudinal axes 500a, 502a of the inserter tool and the anchor 502 releasably coupled to the inserter tool to facilitate suture 126 capture prior to securing the suture 126 in bone with the anchor 502. The suture 126 of FIGS. 8 and 9 is shown in FIG. 24 but another suture can be used. The inner shaft 510 also does not need to be advanced distally to push the suture 126 out of the anchor's slot 504. Additionally, the inner shaft 510 in this illustrated embodiment includes only a single distal arm 522. A single distal arm 522 may effectively capture the suture 126 in the anchor's slot 504 such that two distal arms are not needed.

The anchor 502 is configured and used similar to the anchor 102 of FIGS. 1-4, 8, 9, and 12-14 except that the anchor 502 includes a single slot 504. Although not shown in FIG. 24, the anchor 502 includes bone-engaging features.

In this illustrated embodiment, the slot 504 is formed as a proximally-sloped notch formed in the anchor 502.

The inserter tool and the anchor 502 are generally used similar to the inserter tools and anchors described above. The suture 126 is configured to be seated in the slot 504 of the anchor 502 prior to the anchor 502 being advanced into a patient's body, similar to embodiments discussed above. However, in this illustrated embodiment, with the suture 126 seated in the slot 504, the inner shaft 510 is configured to move axially in a distal direction to capture and lock the suture 126 in the slot 504 with the distal arm 522 of the inner shaft 510 aligned with the slot 504. The inner shaft 510 being in its distal position obstructs the slot 504 to capture and lock the suture 126 therein, similar to that discussed above. The inner shaft 510 is not located distally beyond the anchor 502 prior to the anchor 502 being advanced distally into a bone hole. Instead, after the anchor 502 has been advanced distally into a bone hole, the inner shaft 510 is moved axially in a proximal direction, e.g., with a remainder of the inserter tool, to remove the inner shaft 510 from within the anchor 502 while the anchor 502 and the suture 126 remain secured in the bone hole. The inner shaft 510 can be moved proximally after the anchor 502 has been advanced into a patient's body and prior to the anchor 502 being secured in the bone hole to allow the suture 126 to be tensioned.

One skilled in the art will appreciate further features and advantages of the devices, systems, and methods based on the above-described embodiments. Accordingly, this disclosure is not to be limited by what has been particularly shown and described, except as indicated by the appended claims. All publications and references cited herein are expressly incorporated herein by reference in their entirety for all purposes.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical system, comprising:
   an anchor configured to be implanted in a bone hole, the anchor having a pair of slots formed therein; and
   an inserter tool including an outer shaft and an inner shaft, the anchor being configured to be releasably coupled to the inserter tool;
   wherein with the anchor releasably coupled to the inserter tool, the inner shaft is configured to selectively be in one of a first position, in which the inner shaft obstructs the pair of slots, and a second position, in which the inner shaft does not obstruct the pair of slots;
   in the first position the inner shaft does not extend distally beyond the anchor;
   the anchor releasably coupled to inserter tool is configured to be advanced into the bone hole with the inner shaft in the second position; and
   the inner shaft in the second position is configured to extend distally beyond the anchor and the outer shaft and, thereafter, the outer shaft is configured to translate axially in a distal direction relative to the inner shaft and thereby cause the anchor to translate axially in the distal direction into the bone hole wherein the anchor is configured to be releasably coupled to a suture with the suture extending through the slots of the anchor and being seated in a suture retention channel of the inner shaft;
   the suture is in a locked position relative to the anchor with the inner shaft being in the first position; and
   the inner shaft changing from the first position to the second position is configured to cause the suture to move from the locked position to an unlocked position relative to the anchor;
   wherein each of the slots has an open distal end and a closed proximal end;
   the inner shaft changing from the second position to the first position is configured to cause the inner shaft to push the suture in the slots away from the open distal ends of the slots and toward the closed proximal ends of the slots; and
   the inner shaft in the second position is configured to move distally relative to the anchor and thereby cause the suture to exit the slots by moving away from the closed proximal ends of the slots and moving through the open distal ends of the slots.

2. The system of claim 1, wherein the inner shaft in the second position translating axially in the distal direction is configured to push the suture out of the slots.

3. The system of claim 1, wherein each of the slots has an L-shape or each of the slots has a helical shape.

4. The system of claim 1, wherein the inner shaft has a pair of distal arms;
   the anchor has a pair of distal arms;
   with the inner shaft in the first position, the distal arms of the inner shaft are misaligned from the distal arms of the anchor; and
   with the inner shaft in the second position, the distal arms of the inner shaft are aligned with the distal arms of the anchor.

5. The system of claim 1, wherein the inner shaft has a pair of distal arms;
   with the inner shaft in the first position, the distal arms of the inner shaft are aligned with the slots of the anchor; and
   with the inner shaft in the second position, the distal arms of the inner shaft are misaligned from the slots of the anchor.

6. The system of claim 1, wherein, after the translation of the outer shaft, the outer shaft and the inner shaft are configured to simultaneously translate axially in a proximal direction relative to the anchor in the bone hole.

7. A surgical system, comprising:
   an anchor configured to be implanted in a bone hole, the anchor having a pair of distal arms that define a pair of slots therebetween, the pair of slots is configured to seat a suture therein;
   an inner shaft configured to be seated in an inner lumen of the anchor; and
   an outer shaft configured to longitudinally translate distally relative to the inner shaft and the anchor and thereby move the anchor distally into the bone hole;
   wherein the inner shaft has a pair of distal arms; and
   the anchor is configured to be rotated relative to the inner shaft with the inner shaft within the inner lumen of the anchor and thereby cause:
   the distal arms of the inner shaft to change from being aligned with the distal arms of the anchor and misaligned from the slots of the anchor to being misaligned from the distal arms of the anchor and aligned with the slots of the anchor, and
   the suture to move proximally in the pair of slots.

8. The system of claim 7, wherein the inner shaft is configured to longitudinally move into the bone hole prior to the outer shaft being longitudinally translated distally relative to the inner shaft and the anchor.

9. The system of claim 8, wherein the anchor is configured to be rotated relative to the inner shaft prior to the outer shaft being longitudinally translated distally relative to the inner shaft and the anchor; and the longitudinal movement of the inner shaft is configured to push the suture seated in the slots of the anchor out of the slots and into the bone hole.

10. The system of claim 7, wherein the anchor is configured to be releasably coupled to the suture with the suture extending through the slots of the anchor and being seated in a suture retention channel of the inner shaft;

the suture is in a locked position relative to the anchor with the distal arms of the inner shaft being misaligned from the distal arms of the anchor and aligned with the slots of the anchor; and the suture is in an unlocked position relative to the anchor with the distal arms of the inner shaft being aligned with the distal arms of the anchor and misaligned from the slots of the anchor.

11. The system of claim 7, further comprising the suture.

12. The system of claim 7, wherein, prior to the distal translation of the outer shaft, a distal end of the outer shaft abuts a proximal end of the anchor having the inner shaft positioned within the inner lumen thereof.

13. A surgical method, comprising:

rotating the outer shaft of the inserter tool of the surgical system of claim 1 and the anchor of the surgical system of claim 1 releasably coupled to the inserter tool relative to the inner shaft of the inserter tool, the rotation of the outer shaft and the anchor causing the suture extending through the pair of slots of the anchor to move from a locked position to an unlocked position, the rotation of the outer shaft and the anchor causing the suture to be pushed out of the pair of slots and into the bone hole; and after the rotation of the outer shaft and the anchor, longitudinally translating the outer shaft distally relative to the inner shaft, thereby pushing the anchor into the bone hole to secure the anchor therein.

14. The method of claim 13, wherein the rotation of the outer shaft and the anchor is in a first direction; and the method further comprises, prior to the rotation of the outer shaft and the anchor in the first direction, rotating the outer shaft and the anchor in a second direction that is opposite to the first direction, the rotation of the outer shaft and the anchor in the second direction being relative to the inner shaft, and the rotation of the outer shaft and the anchor in the second direction causing the suture extending through the pair of slots of the anchor to move from the unlocked position to the locked position.

15. The method of claim 13, wherein the rotation of the outer shaft and the anchor in the first direction causes distal arms of the inner shaft to change from being aligned with the pair of slots of the anchor to being misaligned from the pair of slots of the anchor.

\* \* \* \* \*